United States Patent
Rathjen et al.

(10) Patent No.: US 6,593,458 B1
(45) Date of Patent: Jul. 15, 2003

(54) TUMOR NECROSIS FACTOR PEPTIDE BINDING ANTIBODIES

(75) Inventors: Deborah Ann Rathjen, New South Wales (AU); Roger Aston, Gloucester (GB)

(73) Assignee: Peptech Limited (AU)

(*) Notice: Subject to any disclaimer, the term of this patent is extended or adjusted under 35 U.S.C. 154(b) by 0 days.

(21) Appl. No.: 09/736,630

(22) Filed: Dec. 13, 2000

Related U.S. Application Data

(63) Continuation of application No. 09/364,039, filed on Jul. 30, 1999, now Pat. No. 6,416,757, which is a continuation of application No. 08/823,893, filed on Mar. 17, 1997, now Pat. No. 5,959,087, which is a continuation of application No. 08/344,133, filed on Nov. 23, 1994, now Pat. No. 5,644,034, which is a continuation-in-part of application No. 07/828,956, filed as application No. PCT/AU90/00337 on Aug. 7, 1990, now abandoned.

(30) Foreign Application Priority Data

| Aug. 7, 1989 | (AU) | ............................................... PJ5662 |
| Nov. 24, 1989 | (AU) | ............................................... PJ7576 |
| Aug. 7, 1990 | (AU) | ............................... PCT/AU90/00337 |

(51) Int. Cl.$^7$ .......................... C07K 16/00; C07K 16/24
(52) U.S. Cl. .............................. 530/387.9; 530/387.1; 530/388.1; 530/388.2; 530/388.23; 530/389.1; 530/389.2
(58) Field of Search .......................... 530/387.1, 387.9, 530/388.1, 388.2, 388.23, 389.1, 389.2, 300, 326, 351

(56) References Cited

U.S. PATENT DOCUMENTS

| 4,870,163 | A |   | 9/1989 | Rubin et al. |
| 5,075,236 | A |   | 12/1991 | Yone et al. |
| 5,360,716 | A |   | 11/1994 | Ohmoto et al. |
| 5,395,760 | A |   | 3/1995 | Smith et al. |
| 5,644,034 | A |   | 7/1997 | Rathjen et al. |
| 5,658,803 | A |   | 8/1997 | Kuo |
| 5,698,419 | A |   | 12/1997 | Wolpe et al. |
| 5,795,967 | A |   | 8/1998 | Aggarwal et al. |
| 5,959,087 | A |   | 9/1999 | Rathjen et al. |
| 6,416,757 | B1 | * | 7/2002 | Rathjen et al. |
| 6,448,380 | B2 | * | 9/2002 | Rathjen et al. |
| 6,451,983 | B2 | * | 9/2002 | Rathjen et al. |
| 6,498,237 | B2 | * | 12/2002 | Rathjen et al. |

FOREIGN PATENT DOCUMENTS

| WO | WO 91/02078 | 2/1991 |

OTHER PUBLICATIONS

Fendly et al. (1987). "Murine Monoclonal Antibodies Defining Neutralizing Epitopes on Tumor Necrosis Factor," *Hybridoma* 6(4):359–370.

Hirai et al. (1987). "Production and Characterization of Monoclonal Antibodies to Human Tumor Necrosis Factor," *J. Immunol. Meth*. 96:57–62.

Liang et al. (1986). "Production and Characterization of Monoclonal Antibodies Against Recombinant Human Tumor Necrosis Factor/Cachectin," *Biochem. Biophys. Res. Comm*. 137(2):847–854.

Meager et al. (1987). "Preparation and Characterization of Monoclonal Antibodies Directed Against Antigenic Determinants of Recombinant Human Tumour Necrosis Factor (rTNF)," *Hybridoma* 6(3):305–311.

Yamauchi et al. (1989). "Intracellular Hydroxyl Radical Production Induced by Recombinant Human Tumor Necrosis Factor and Its Implication in the Killing of Tumor Cell In Vitro," *Cancer Res*. 49:1671–1675.

Aston, R. et al. (1985) "Monoclonal antibodies to growth hormone and prolactin" *Pharmac. Therapeut*. 27:403–424.

Aston, R. et al. (1989) "Antibody–mediated enhancement of hormone activity," *Mol. Immunol*. 26(5):435–446.

Bevilacqua, M.P. et al. (Jun. 1986). "Recombinant tumor necrosis factor induces procoagulant activity in cultured human vascular endothelium: characterization and comparison with the actions of interleukin 1," *Proc. Natl. Acad. Sci. USA* Medical Sciences 83:4533–4537.

Bringman, t. and Aggarwal, B.B. (1987) "Monoclonal antibodies to human tumor necrosis factors alpha and beta: application for affinity purification, immunoassays, and as structural probes" *Hybridoma* 6(5):489–507.

Espevik, T. and Nissen–Meyer, J. (1986). "A highly sensitive cell line, WEHI 164 clone 13, for measuring cytotoxic factor/tumor necrosis factor from human monocytes," *J. Immunol. Methods* 95:99–105.

Geysen, H.M. et al. (Jul. 1984). "Use of peptide synthesis to probe viral antigens for epitopes to a resolution of a single amino acid" *Proc. Natl. Acad. Sci*. 81:3998–4002.

Kabat, E.A. (1991) *Sequences of Proteins of Immunological Interest*, 5th Edition, from *US Public Health Services*, NIH publication No. 91–3242, Table of Contents, pp. iii–xi.

Marks, J.D. et al. (1991). "Oligonucleotide primers for polymerase chain reaction amplification of human immunoglobulin variable genes and design of family–specific oligonucleotide probes" *Eur. J. Immunol*. 21(4):985–991.

(List continued on next page.)

Primary Examiner—Phillip Gambel
Assistant Examiner—Jessica H. Roark
(74) Attorney, Agent, or Firm—Morrison & Foerster LLP

(57) ABSTRACT

Provided are isolated antibodies or fragments thereof which bind a peptide consisting of residues $Leu_{63}$-$Phe_{64}$-$Lys_{65}$-$Gly_{66}$-$Gln_{67}$-$Gly_{68}$-$Cys_{69}$-$Pro_{70}$-$Ser_{71}$-$Thr_{72}$-$His_{73}$-$Val_{74}$-$Leu_{75}$-$Leu_{76}$-$Thr_{77}$-$His_{78}$-$Thr_{79}$-$Ile_{80}$-$Ser_{81}$-$Arg_{82}$-$Ile_{83}$ (peptide 304) of mature human TNF-α. The antibodies and fragments thereof may be used to identify antibodies capable of binding in the region of mature human TNF-α of amino acid resides 63–83. Antibodies or fragments thereof which bind particular regions of mature human TNF-α are shown to elicit particular biological activities dependent upon the particular region wherein binding occurs.

1 Claim, 28 Drawing Sheets

OTHER PUBLICATIONS

Natanson, C. et al., (1994) "Selected treatment strategies for septic shock based on proposed mechanisms of pathogenesis" *Ann. Int. Med.*, 120(9):771–783.

Neda, H. (1987) "Analysis of the tumor necrosis factor (TNF) receptor of various tumor cells" *Sapporo Med J.* 56(2):305–317.

Pennica, D. et al., (1984) "Human tumour necrosis factor: precursor structure, expression and homology to lymphotoxin" *Nature* 312:724–729.

Rathjen, D.A. and Underwood, P.A. (1986) "Identification of antigenic determinants on insulin recognized by monoclonal antibodies" *Mol. Immunol.* 23(4):441–450.

Socher, S.H. et al. (Dec. 1987) "Antibodies against amino acids 1–15 tumor necrosis factor block its binding to cell–surface receptor" *Proc. Natl. Acad. Sci. USA* Biochemistry 84:8829–8833.

Tomlinson, I.M. et al. (1992) "The repertoire of human germline $V_H$ sequences reveals about fifty groups of $V_H$ segments with different hypervariable loops" *J. Mol. Biol.* 227:776–798.

Tracey, K.J. et al., (1987) "Anti–cachectin/TNF monoclonal antibodies prevent septic shock during lethal bacteraemia" *Nature* 330:662–664.

Watanabe, N. et al., (1986) "Analysis of the TNF receptors of kym cells by affinity cross–linking" Japanese article from Gan To Kagaku Ryoho (*Jpn. J. Cancer Chemotherapy*) 13(8):2625–2629, and English translation, 5 pages.

Watanabe, N. et al. (1988) "Synergistic cytotoxicity of recombinant human TNF and various anticancer drugs" *Immunopharmacol. Immunotoxicol.* 10(1):117–127.

Zwierzina, H. (1993) "Practical aspects of cytokine therapy" *Stem Cells* 11:144–153.

* cited by examiner

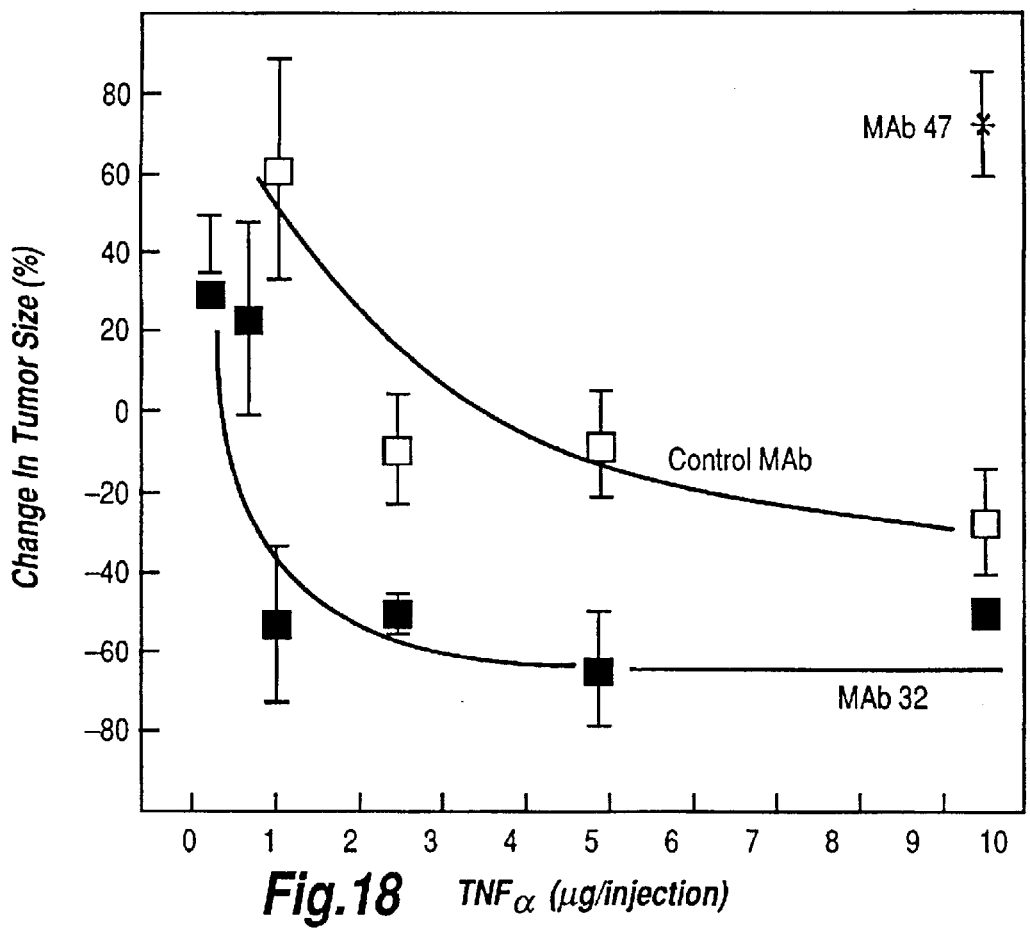
Fig. 18 TNFα (μg/injection)
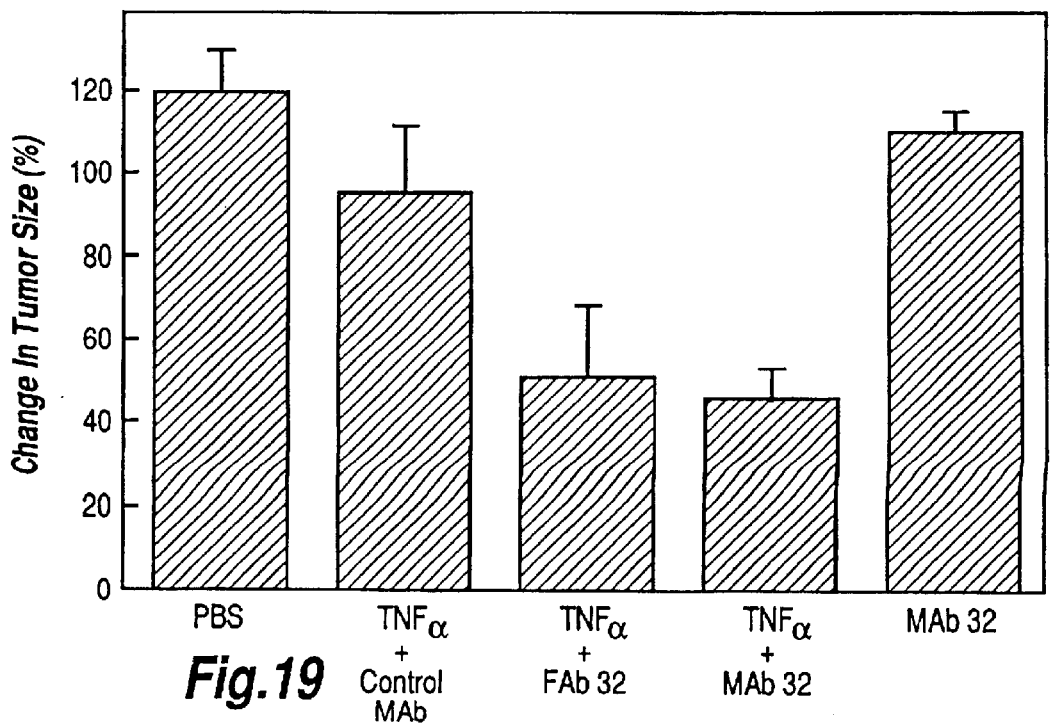
Fig. 19

PEPTIDE NUMBER

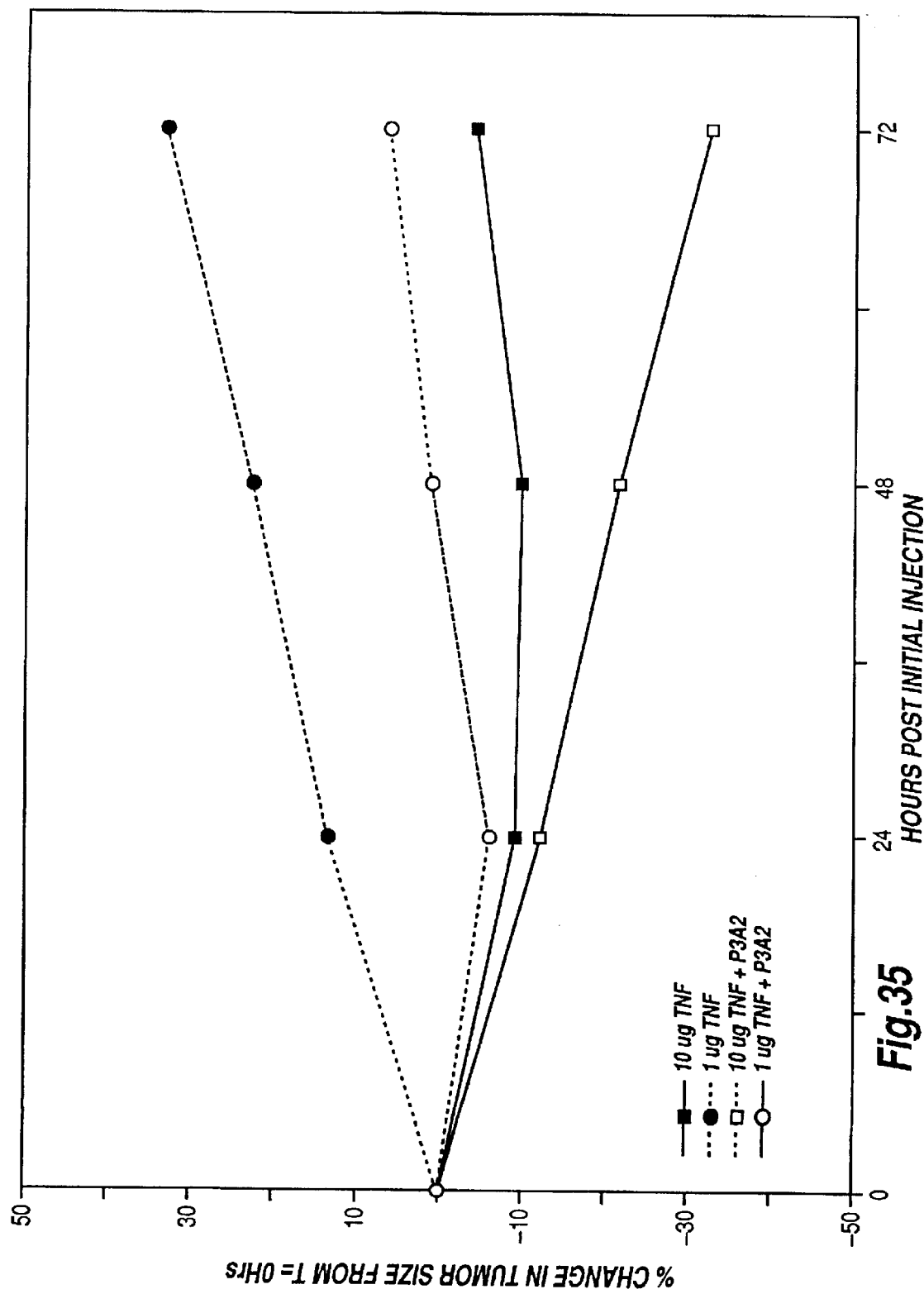

TUMOR NECROSIS FACTOR PEPTIDE BINDING ANTIBODIES

This application is a continuation of application Ser. No. 09/364,039, filed Jul. 30, 1999 (now U.S. Pat. No. 6,416, 757), which is a continuation of application Ser. No. 08/823, 893, filed Mar. 17, 1997 (now U.S. Pat. No. 5,959,087), which is a continuation of application Ser. No. 08/344,133, filed Nov. 23, 1994 (now U.S. Pat. No. 5,644,034), which is a continuation-in-part of application Ser. No. 07/828,956, filed Feb. 18, 1992 (now abandoned), which is a national phase filing of PCT/AU90/00337, filed Aug. 7, 1990, and published, in English, as International Publication No. WO 91/02078 on Feb. 21, 1991, designating the United States, which claims the benefit of Australian applications AU PJ5662, filed Aug. 7, 1989, and AU PJ7576, filed Nov. 24, 1989, the disclosures of which are incorporated herein by reference in their entirety.

FIELD OF THE INVENTION

The present invention relates to ligands which bind to human tumour necrosis factor alpha (TNF) in a manner such that upon binding the biological activity of TNF is modified. The type of modification shown here is distinct from previous descriptions of antibodies which bind to TNF alpha and inhibit all TNF alpha activity. The new discovery shows how the different activities of TNF alpha can be selectively inhibited or enhanced. In addition, the present invention relates to a composition comprising a molecule bound to TNF and to methods of therapy utilising TNF and molecules active against TNF.

BACKGROUND OF THE INVENTION

Tumor necrosis factor alpha (TNF) is a product of activated macrophages first observed in the serum of experimental animals presensitized with *Bacillus Calmette-Guerin* or *Corynebacterium parvum* and challenged with endotoxin (LPS). Following the systematic administration of TNF haemorrhagic necrosis was observed in some transplantable tumours of mice while in vitro TNF caused cytolytic or cytostatic effects on tumour cell lines.

In addition to its host-protective effect, TNF has been implicated as the causative agent of pathological changes in septicemia, cachexia and cerebral malaria. Passive immunization of mice with a polyclonal rabbit serum against TNF has been shown to protect mice against the lethal effects of LPS endotoxin, the initiating agent of toxic shock, when administered prior to infection.

The gene encoding TNF has been cloned allowing the usefulness of this monokine as a potential cancer therapy agent to be assessed. While TNF infusion into cancer patients in stage 1 clinical trials has resulted in tumour regression, side-effects such as thrombocytopaenia, lymphocytopaenia, hepatotoxicity, renal impairment and hypertension have also been reported. These quite significant side-effects associated with the clinical use of TNF are predictable in view of the many known effects of TNF, some of which are listed in Table 1.

TABLE 1

BIOLOGICAL ACTIVITIES OF TNF

-ANTI-TUMOUR
-ANTI-VIRAL
-ANTI-PARASITE
FUNCTION cytotoxic action on tumour cells
pyrogenic activity TABLE 1-continued

BIOLOGICAL ACTIVITIES OF TNF angiogenic activity
inhibition of lipoprotein lipase
activation of neutrophils
osteoclast activation
induction of endothelial, monocyte and tumour cell procoagulant activity
induction of surface antigens on endothelial cells
induction of IL-6
induction of c-myc and c-fos
induction of EGF receptor
induction of IL-1
induction of TNF synthesis
induction of GM-CSF synthesis
increased prostaglandin and collagenase synthesis
induction of acute phase protein C3

Of particular importance is the activation of coagulation which occurs as a consequence of TNF activation of endothelium and also peripheral blood monocytes. Disseminated intravascular coagulation is associated with toxic shock and many cancers including gastro-intestinal cancer, cancer of the pancreas, prostate, lung, breast and ovary, melanoma, acute leukaemia, myeloma, myeloproliferative syndrome and myeloblastic leukaemia. Clearly modifications of TNF activity such that tumour regression activity remains intact but other undesirable effects such as activation of coagulation are removed or masked would lead to a more advantageous cancer therapy, while complete abrogation of TNF activity is sought for successful treatment of toxic shock.

Segregation of hormonal activity through the use of site-specific antibodies (both polyclonal and monoclonal) can result in enhanced hormonal activity (Aston et al, 1989, Mol. Immunol. 26, 435). To date few attempts have been made to assign antigenicity or function to particular regions of the TNF molecule for which the three-dimensional structure is now known. Assignment of function to such regions would permit the development of MAbs and other ligands of therapeutic use. Polyclonal antibodies to amino acids 1 to 15 have been reported to block Hela R19 cell receptor binding by TNF (Socher et al, 1987, PNAS 84, 6829) whilst monoclonal antibodies recognising undefined conformational epitopes on TNF have been-shown to inhibit TNF cytotoxicity in vitro (Bringman and Aggarwal, 1987, Hybridoma 6, 489). However, the effects of these antibodies on other TNF activities is unknown.

SUMMARY OF THE PRESENT INVENTION

The present inventors have produced panels of monoclonal antibodies active against human TNF and have characterised them with respect to their effects on the anti-tumour effect of TNF (both in vitro and in vivo), TNF receptor binding, activation of coagulation (both in vitro and in vivo) and defined their topographic specificities. This approach has led the inventors to show that different topographic regions of TNF alpha are associated with different activities. Therefore the inventors enable the identification of antibodies or ligands which selectively enhance or inhibit TNF alpha activity, thereby providing for improved therapeutic agents and regimes including TNF alpha.

In a first aspect the present invention consists in a ligand capable of binding to human TNF, the ligand being characterised in that when it binds to TNF the following biological activities of the TNF are inhibited:

1. Tumour regression;
2. Induction of endothelial procoagulant;
3. Induction of tumour fibrin deposition;
4. Cytotoxicity; and
5. Receptor binding.

In a preferred embodiment of all aspects the present invention the ligand is selected from the group consisting of antibodies, F(ab) fragments, restructured antibodies (CDR grafted humanised antibodies) single domain antibodies (dAbs), single chain antibodies, serum binding proteins, receptors and natural inhibitors. The ligand may also be a protein or peptide which has been synthesised and which is analogous to one of the foregoing fragments. However, it is presently preferred that the ligand is a monoclonal antibody or F(ab) fragment thereof.

In a second aspect the present invention consists in a ligand capable of binding to human TNF, the ligand being characterized in that when it binds to TNF the induction of endothelial procoagulant, tumour regression, induction of tumour fibrin deposition, cytotoxicity and receptor binding activities of the TNF are inhibited, the ligand binding to the TNF such that the epitope of the TNF defined by the topographic regions of residues 1–18, 58–65, 115–125 and 138–149, or the topographic region of residues 1–18, 108–128, or the topographic region of residues 56–79, 110–127 and 135–155 is substantially prevented from binding to naturally occurring biologically active ligands.

In a third aspect the present invention consists in a ligand which binds to human TNF in at least two regions selected from the group consisting predominantly of the topographic region of residues 1–20, the topographic region of residues 56–77, the topographic region of residues 108–127 and the topographic region of residues 138–149.

In a preferred embodiment of the third aspect of the present invention the ligand binds to human TNF in the topographic regions of residues 1–18, 58–65, 115–125 and 138–149. Such sequence regions are topographically represented in FIG. 23.

In a further preferred embodiment of the third aspect of the present invention the ligand binds to human TNF in the topographic regions of residues 1–18 and 108–128. Such sequence regions are topographically represented in FIG. 24.

In a further preferred embodiment of the second aspect of the present invention the ligand binds to human TNF in the topographic regions of residues 56–79, 110–127 and 136–155. Such sequence regions are topographically represented in FIG. 25.

In a particularly preferred embodiment of the first, second and third aspects of the present invention the ligand is a monoclonal antibody selected from the group consisting of the monoclonal antibodies designated MAb 1, MAb, 47 and MAb 54. Samples of the hybridoma cell lines which produce MAb 1, MAb 54 and MAb 47 have been deposited with the European Collection of Animal Cell Cultures (ECACC), Vaccine Research and Production Laboratory, Public Health Laboratory Service, Centre for Applied Microbiology and Research, Porton Down, Salisbury, Wiltshire SP4 OJG, United Kingdom. MAb 1 was deposited on Aug. 3, 1989 and accorded accession No. 89080301; MAb 54 was deposited on Aug. 31, 1989 and accorded accession No. 89083103; MAb 47 was deposited on Dec. 14, 1989 and accorded accession No. 89121402.

In a fourth aspect the present invention consists in a composition comprising TNF in combination with the ligand of the first, second or third aspect of the present invention, characterised in that the ligand is bound to the TNF.

In a fifth aspect the present invention consists in a method of treating toxic shock comprising administering either the ligand of the first, second or third aspect of the present invention or the composition of the fourth aspect of the present invention.

In a sixth aspect the present invention consists in a ligand capable of binding to human TNF, the ligand being characterised in that when it binds to TNF the induction of endothelial procoagulant activity of the TNF is inhibited; binding of TNF to receptors on endothelial cells is inhibited; the induction of tumour fibrin deposition and tumour regression activities of the TNF are enhanced; the cytotoxicity is unaffected and tumour receptor binding activities of the TNF are unaffected or enhanced.

In a seventh aspect the present invention consists in a ligand capable of binding to human TNF, the ligand being characterized in that when it binds to TNF the induction of endothelial procoagulant activity of the TNF is inhibited; the binding of the TNF to receptors on endothelial cells is inhibited, the induction of tumour fibrin deposition and tumour regression activities of the TNF are enhanced; and the cytotoxicity and receptor binding activities of the TNF are unaffected; the ligand binding to the TNF such that the epitope of the TNF defined by the topographic regions of residues 1–30, 117–128 and 141–153 is substantially prevented from binding to naturally occurring biologically active ligands.

In an eighth aspect the present invention consists of a ligand which binds to human TNF in the topographic regions of residues 1–30, 117–128 and 141–153.

In a preferred embodiment of the eighth aspect of the present invention the ligand binds to human TNF in the topographic regions of residues 1–26, 117–128 and 141–153. Such sequence regions are topographically represented in FIG. 26.

In a preferred embodiment of the sixth, seventh and eighth aspects of the present invention the ligand is the monoclonal antibody designated MAb 32. A sample of the hybridoma producing MAb 32 was deposited with The European Collection of Animal Cell Cultures (ECACC), Vaccine Research and Production Laboratory, Public Health Laboratory Service, Centre for Applied Microbiology and Research, Porton Down, Salisbury, Wiltshire SP4 OJG, United Kingdom on Aug. 3, 1989 and was accorded accession No. 89080302 under the terms and conditions of the Budapest Treaty for the Deposit of Microorganisms for Patent process.

In a ninth aspect the present invention consists in a composition comprising TNF in combination with a ligand of the sixth, seventh or eighth aspects of the present invention characterised in that the ligand is bound to TNF. No previous documentation of administering MAbs with TNF in order to modify activity of the administered cytokine exists.

In a tenth aspect the present invention consists in a method of treating tumours the growth of which is inhibited by TNF, comprising administering either the ligand of the sixth, seventh or eighth aspects of the present invention or the composition of the ninth aspect of the present invention.

In an eleventh aspect the present invention consists in a ligand which binds to residues 1–18 of human TNF (peptide 301).

In a twelfth aspect the present invention consists in a ligand capable of binding to human TNF, the ligand being characterized in that when it binds to TNF the induction of endothelial procoagulant activity of the TNF is inhibited; the binding of TNF to receptors on endothelial cells is inhibited; the induction of tumour fibrin deposition and tumour regression activities of the TNF are enhanced; the cytotoxicity of the TNF are unaffected and tumour receptor binding activities of the TNF are unaffected or enhanced, the ligand binding to TNF such that the epitope of the TNF defined by the topographic region of residues 1–18 is substantially prevented from binding to naturally occurring biologically active ligands.

In a thirteenth aspect the present invention consists in a composition comprising TNF in combination with a ligand of the eleventh or twelfth aspects of the present invention characterized in that the ligand is bound to the TNF.

In a fourteenth aspect the present invention consists in a method of treating tumours the growth of which is inhibited by TNF, comprising administering either the ligand of the eleventh or twelfth aspect of the present invention or the composition of the thirteenth aspect of the present invention.

In a fifteenth aspect the present invention consists in a ligand capable of binding to human TNF, the ligand being characterised in that when it binds to TNF the cytotoxicity and tumour regression activities of the TNF are unaffected; the induction of endothelial procoagulant and induction of tumour fibrin deposition activities of the TNF are inhibited and receptor binding activities of the TNF are unaffected.

In a sixteenth aspect the present invention consists in a ligand capable of binding to human TNF, the ligand being characterized in that when it binds to TNF the cytotoxicity and tumour regression activities of the TNF are unaffected; the induction of endothelial procoagulant and induction of tumour fibrin deposition activities of the TNF are inhibited and the tumour receptor binding activities of the TNF are unaffected, the ligand binding to TNF such that the epitope of the TNF defined by the topographic regions of residues 22–40, 49–97, 110–127 and 136–153 is substantially prevented from binding to naturally occurring biologically active ligands.

In a seventeenth aspect the present invention consists in a ligand which binds to human TNF in the topagraphic regions of residues 22–40, 49–97, 110–127 and 136–153. Such sequence regions are topographically represented in FIG. 27.

In a preferred embodiment of the seventeenth aspect of the present invention the ligand binds to human TNF in the topographic regions of residues 22–40, 49–96, 110–127 and 136–153. These regions being proximate in the 3D structure of TNF alpha.

In a preferred embodiment of the fifteenth, sixteenth and seventeenth aspects of the present invention the ligand is the monoclonal antibody designated MAb 42. A sample of the hybridoma cell line producing MAb 42 was deposited with The European Collection of Animal Cell Cultures (ECACC), Vaccine Research and Production Laboratory, Public Health Laboratory Service, Centre for Applied Microbiology and Research, Porton Down, Salisbury, Wiltshire SP4 OJG, United Kingdom on Aug. 3, 1989 and was accorded accession No. 89080304.

In an eighteenth aspect the present invention consists in a composition comprising TNF in combination with the ligand of the fifteenth, sixteenth or seventeenth aspects of the present invention, characterised in that the ligand is bound to the TNF.

In a nineteenth aspect the present invention consists in a method of treating tumours inhibited by the action of TNF comprising administering the ligand of the fifteenth, sixteenth or seventeenth aspects of the present invention or the composition of the eighteenth aspect of the present invention.

In a twentieth aspect the present invention consists in a ligand capable of binding to human TNF, the ligand being characterised in that when it binds to TNF the tumour fibrin deposition activity of the TNF is enhanced; the induction of endothelial procoagulant activity of the TNF is unaffected and the cytotoxicity, tumour regression and receptor binding activities of the TNF are inhibited.

In a twenty-first aspect the present invention consists in a ligand capable of binding to human TNF, the ligand being characterized in that when it binds to TNF the tumour fibrin deposition activity of the TNF is enhanced; the induction of endothelial procoagulant activity of the TNF is unaffected and the cytotoxicity, tumour regression and tumour receptor binding activities of the TNF are inhibited, the ligand binding to TNF such that the epitope of the TNF defined by the topographic regions of residues 12–22, 36–45, 96–105 and 132–157 is substantially prevented from binding to naturally occurring biologically active ligands.

In a twenty-second aspect the present invention consists in a ligand which binds to human TNF in the topographic regions of residues 12–22, 36–45, 96–105 and 132–157. These regions are proximate in the 3D structure of TNF and are topographically represented in FIG. 28.

In a preferred embodiment of the twentieth, twenty-first and twenty-second aspects of the present invention the ligand is the monoclonal antibody designated MAb 25. A sample of the hybridoma cell line producing MAb 25 was deposited with the European Collection of Animal Cell Cultures (ECACC), Vaccine Research and Production Laboratory, Public Health Laboratory Service, Centre for Applied Microbiology and Research, Porton Down, Salisbury, Wiltshire SP4 OJG, United Kingdom on Dec. 14, 1989 and was accorded accession No. 89121401.

In a twenty-third aspect the present invention consists in a ligand capable of binding to human TNF, the ligand being characterised in that when it binds to TNF the tumour fibrin deposition activity of the TNF is enhanced and the cytotoxicity, tumour regression, induction of endothelial procoagulant and receptor binding activities of the TNF are inhibited.

In a twenty-fourth aspect the present invention consists in a ligand capable of binding to human TNF, the ligand being characterized in that when it binds to TNF the tumour fibrin deposition activity of the TNF is enhanced and the cytotoxicity, tumour regression, induction of endothelial procoagulant and tumour receptor binding activities of the TNF are inhibited, the ligand binding to the TNF such that the epitope of the TNF defined by the topographic regions of residues 1–20 and 76–90 is substantially prevented from binding to naturally occurring biologically active ligands.

In a twenty-fifth aspect the present invention consists in a ligand which binds to human TNF in the topographic regions of residues 1–20 and 76–90. These regions are proximate in the 3D structure of TNF and are topographically represented in FIG. 29.

In a preferred embodiment of the twenty-fifth aspect of the present invention the ligand binds to TNF in the topographic regions of residues 1–18 and 76–90.

In a preferred embodiment of the twenty-third, twenty-fourth and twenty-fifth aspects of the present invention the ligand is the monoclonal antibody designated MAb 21. A sample of the hybridoma cell line producing MAb 21 was deposited with the European Collection of Animal Cell Cultures (ECACC), Vaccine Research and Production Laboratory, Public Health Laboratory Service, Centre for Applied Microbiology and Research, Porton Down, Salisbury, Wiltshire SP4 OJG, United Kingdom on Jan. 25, 1990 and was accorded accession No. 90012432.

In a twenty-sixth aspect the present invention consists in a ligand capable of binding to human TNF, the ligand being characterised in that when it binds to TNF the fibrin deposition activity of the TNF is unaffected and the cytotoxicity, tumour regression, induction of endothelial procoagulant and tumour receptor binding activities of the TNF are inhibited.

In a twenty-seventh aspect the present invention consists in a ligand capable of binding to human TNF, the ligand being characterized in that when it binds to TNF the tumour fibrin deposition activity of the TNF is unaffected and the cytotoxicity, tumour regression, induction of endothelial procoagulant and receptor binding activities of the TNF are inhibited, the ligand binding to the TNF such that the epitope of the TNF defined by the topographic regions of residues 22–40, 69–97, 105–128 and 135–155 is substantially prevented from binding to naturally occurring biologically active ligands.

In a twenty-eighth aspect the present invention consists in a ligand which binds to human TNF in the topographic regions of residues 22–40, 69–97, 105–128 and 135–155. These regions are proximate in the 3D structure of TNF and are topographically represented in FIG. 30.

In a preferred embodiment of the twenty-sixth, twenty-seventh and twenty-eighth aspects of the present invention the ligand is the monoclonal antibody designated MAb 53. A sample of the hybridoma cell line producing MAb 53 was deposited with the European Collection of Animal Cell Cultures (ECACC), Vaccine Research and Production Laboratory, Public Health Laboratory Service, Centre for Applied Microbiology and Research, Porton Down, Salisbury, Wiltshire SP4 OJG, United Kingdom on Jan. 25, 1990 and was accorded accession No. 90012433.

In a twenty-ninth aspect the present invention consists in a ligand capable of binding to human TNF, the ligand being characterised in that when it binds to the TNF tumour fibrin deposition, induction of endothelial procoagulant, cytotoxicity, tumour regression and receptor binding activities of the TNF are unaffected.

In a thirtieth aspect the present invention consists in a ligand capable of binding to human TNF, the ligand being characterised in that when it binds to TNF the tumour fibrin deposition, induction of endothelial procoagulant, cytotoxicity, tumour regression and receptor binding activities of the TNF are unaffected, the ligand binding to TNF such that the epitope of the TNF defined by the topographic regions of residues 22–31 and 146–157 is substantially prevented from binding to naturally occurring biologically active ligands.

In a thirty-first aspect the present invention consists in a ligand which binds to human TNF in the topographic regions of residues 22–31 and 146–157. These regions are proximate in the 3D structure of TNF and are typographically represented in FIG. 31.

In a preferred embodiment of the twenty-ninth, thirtieth and thirty-first aspects of the present invention the ligand is the monoclonal antibody designated MAb 37. A sample of the hybridoma cell line producing MAb 37 was deposited with the European Collection of Animal Call Cultures (ECACC), Vaccine Research and Production Laboratory, Public Health Laboratory Service, Centre for Applied Microbiology and Research, Porton Down, Salisbury, Wiltshire SP4 OJG, United Kingdom on Aug. 3, 1989 and was accorded accession No. 89080303.

In a thirty-second aspect the present invention consists in a ligand capable of binding to human TNF, the ligand being characterised in that when it binds to TNF the induction of endothelial procoagulant activity of the TNF is unaffected and the cytotoxicity, tumour regression, tumour fibrin deposition, and receptor binding activities of the TNF are inhibited.

In a thirty-third aspect the present invention consists in a ligand capable of binding to human TNF, the ligand being characterised in that when it binds to TNF the induction of endothelial procoagulant activity of the TNF is unaffected and the cytotoxicity, tumour regression, tumour fibrin deposition and receptor binding activities of the TNF are inhibited, the ligand binding to the TNF such that the epitope of the TNF defined by the topographic regions of residues 22–40 and 49–98 is substantially prevented from binding to naturally occurring biologically active ligands.

In a thirty-fourth aspect the present invention consists in a ligand which binds to human TNF in at least one of the regions selected from the group consisting of the topographic region of residues 22–40, the topographic region of residues 49–98 and the topographic region of residues 69–97.

In a preferred embodiment of the thirty-fourth aspect of the present invention the ligand binds to human TNF in the topographical region of residues 49–98. This region is topographically represented in FIG. 32.

In a further preferred embodiment of the thirty-fourth aspect of the present invention the ligand binds to human TNF in the topographic regions of residues 22–40 and 70–87. These regions are proximate in the 3D structure of TNF and are topographically represented in FIG. 33.

In a preferred embodiment of the thirty-second, thirty-third and thirty-fourth aspects of the present invention the ligand is monoclonal antibody MAb 11 or MAb 12.

In a thirty-fifth aspect the present invention consists in a ligand capable of binding to human TNF, the ligand being characterised in that when it binds to TNF the induction of endothelial procoagulant activity of the TNF is inhibited.

In a thirty-sixth aspect the present invention consists in a ligand capable of binding to human TNF, the ligand being characterised in that when it binds to TNF the induction of endothelial procoagulant activity of the TNF is inhibited, the ligand binding to TNF such that the epitope of the TNF defined by the topographical region of residues 108–128 is prevented from binding to naturally occurring biologically active ligands.

In a thirty-seventh aspect the present invention consists in a ligand which binds to human TNF in the topographical region of residues 108–128.

In a preferred embodiment of the thirty-fifth, thirty-sixth and thirty-seventh aspects of the present invention the ligand is selected from the group consisting of monoclonal antibodies designated MAb 1, MAb 32, MAb 42, MAb 47, MAb 53 and MAb 54.

The biological activities of TNF referred to herein by the terms "Tumour Regression", "Induction of Endothelial Procoagulant", "Induction of Tumour Fibrin Deposition", "Cytotoxicity" and "Receptor Binding" are to be determined by the methods described below.

The term "single domain antibodies" as used herein is used to denote those antibody fragments such as described in Ward et al (Nature, Vol. 341, 1989, 544–546) as suggested by these authors.

In order that the nature of the present invention may be more clearly understood, preferred forms thereof will now be described with reference to the following example and accompanying figures in which:

BRIEF DESCRIPTION OF THE DRAWINGS

FIG. 1 shows the results of a titration assay with MAb 1 against TNF;

FIG. 2 shows TNF MAb 1 scatchard plot and affinity determination;

Figure 11A:
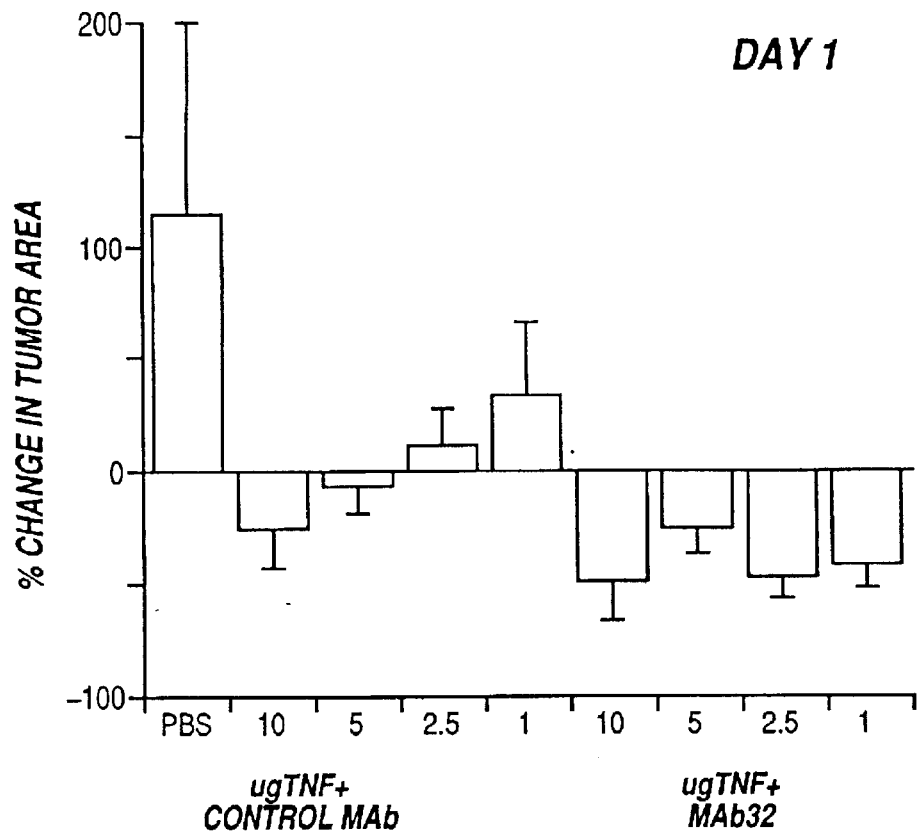
Figure 11B:
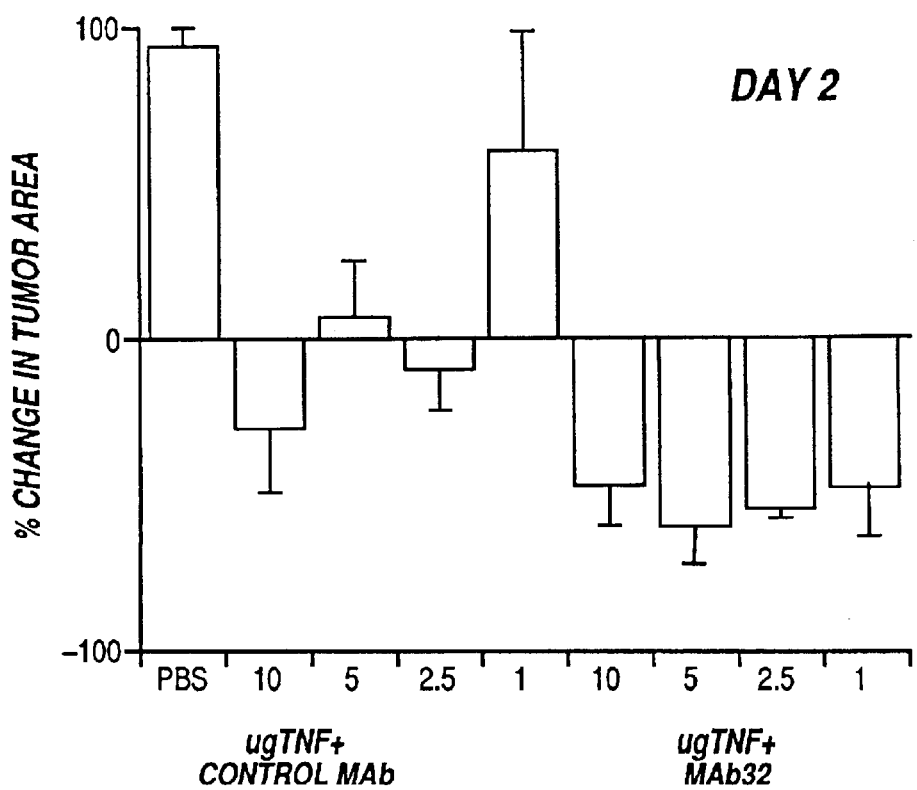
Figure 12:
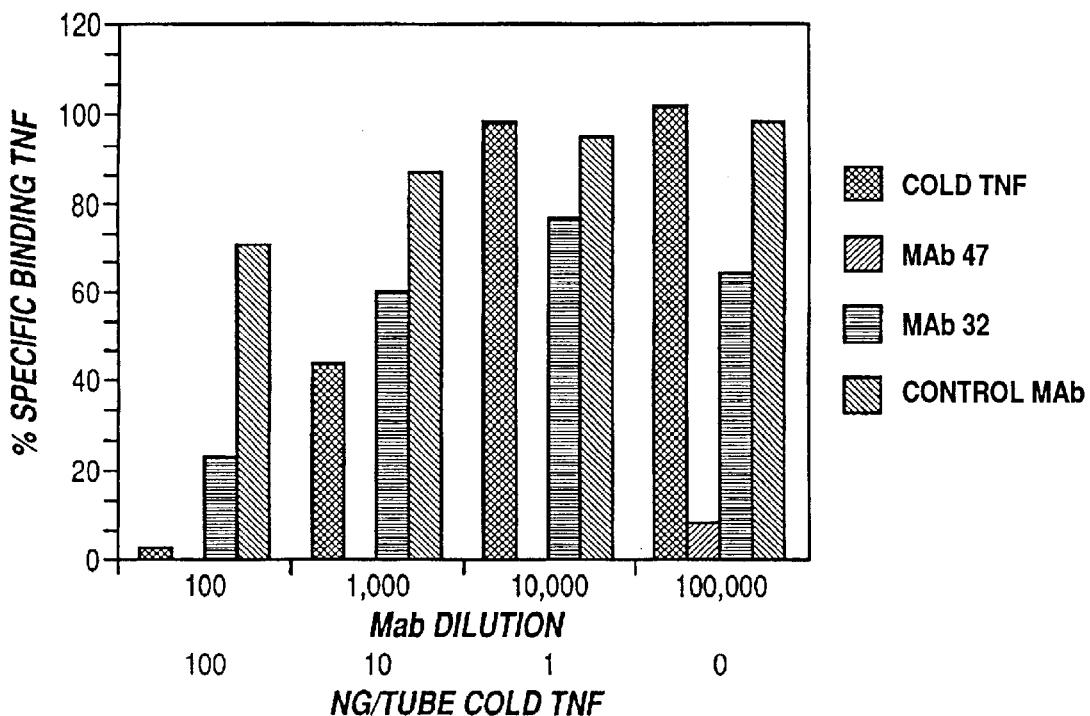
Figure 13:
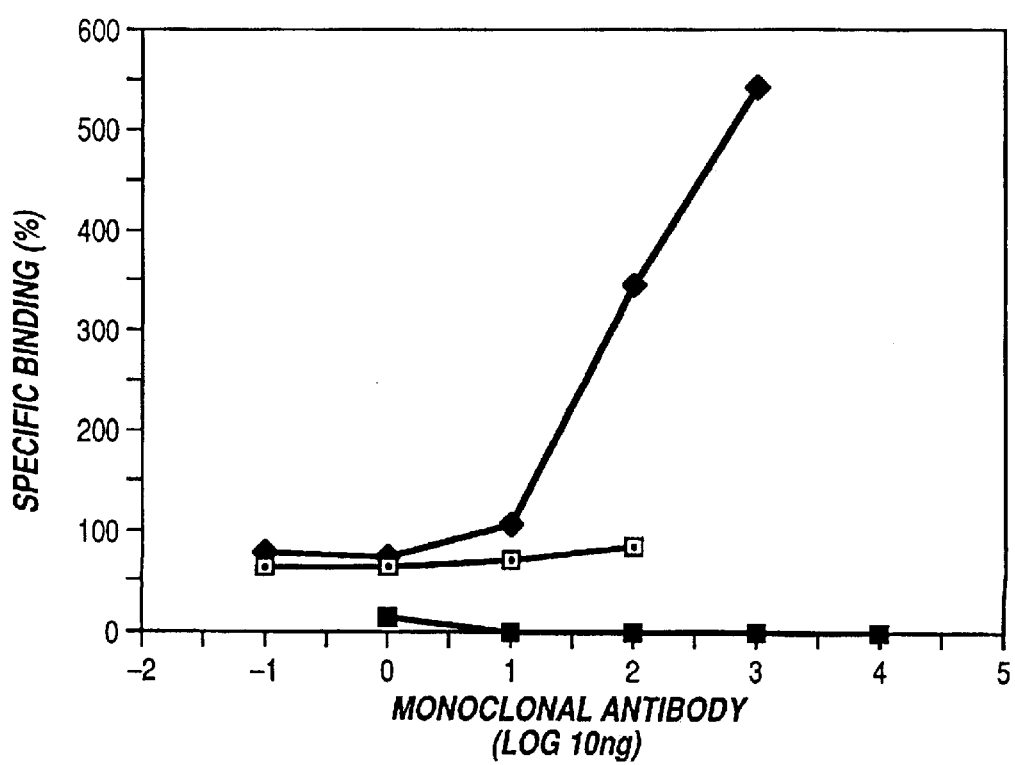
Figure 14:
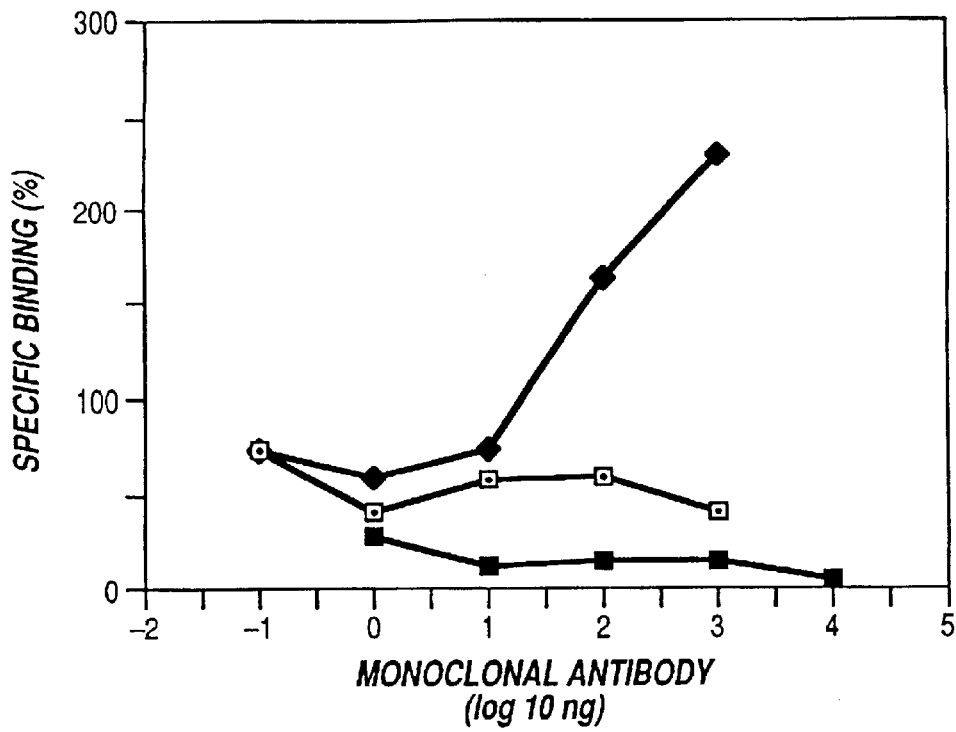
Figure 15:
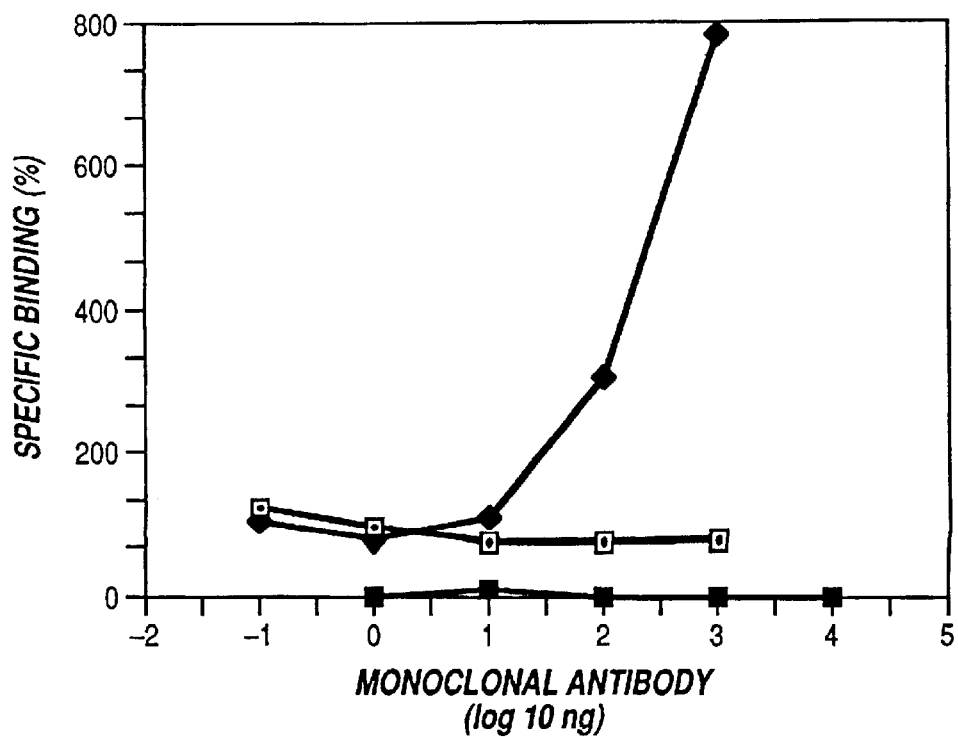
Figure 16:
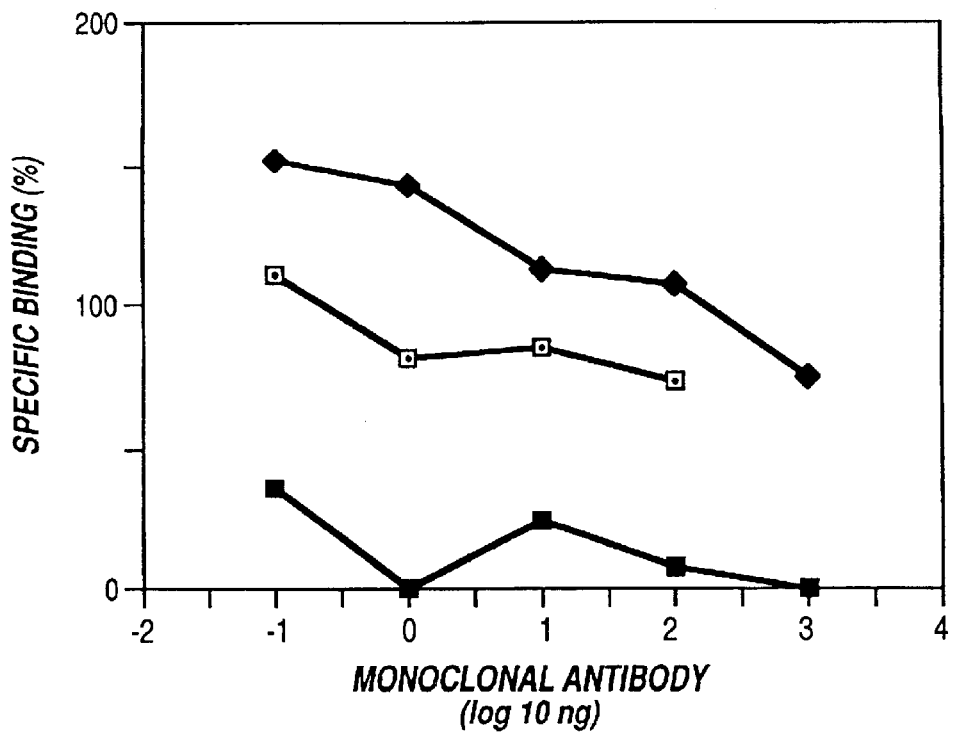
Figure 17:
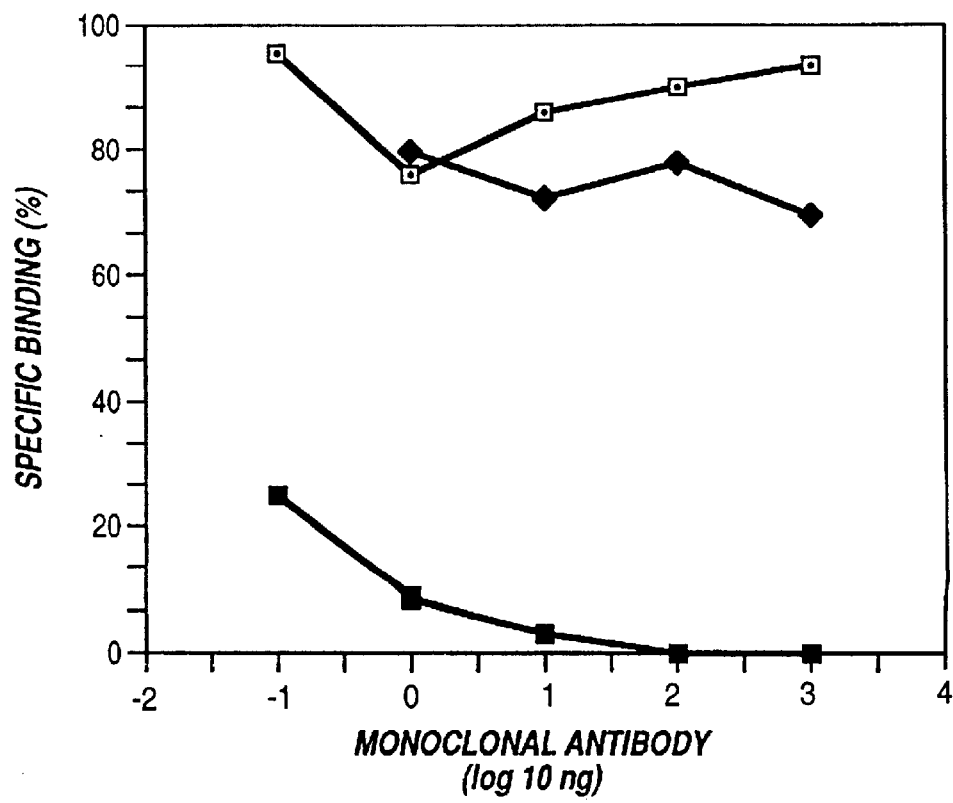
Figure 20:
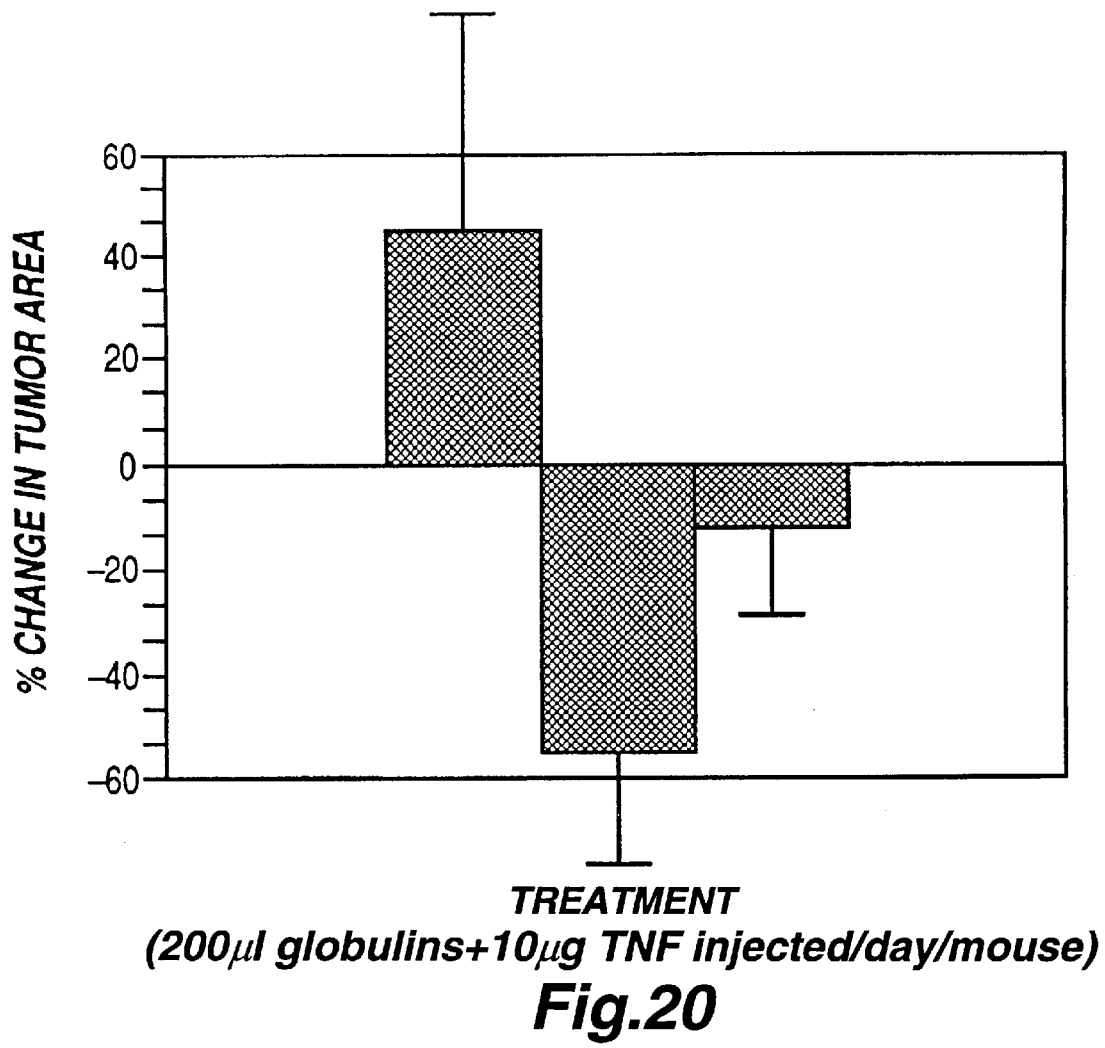
Figure 21A:
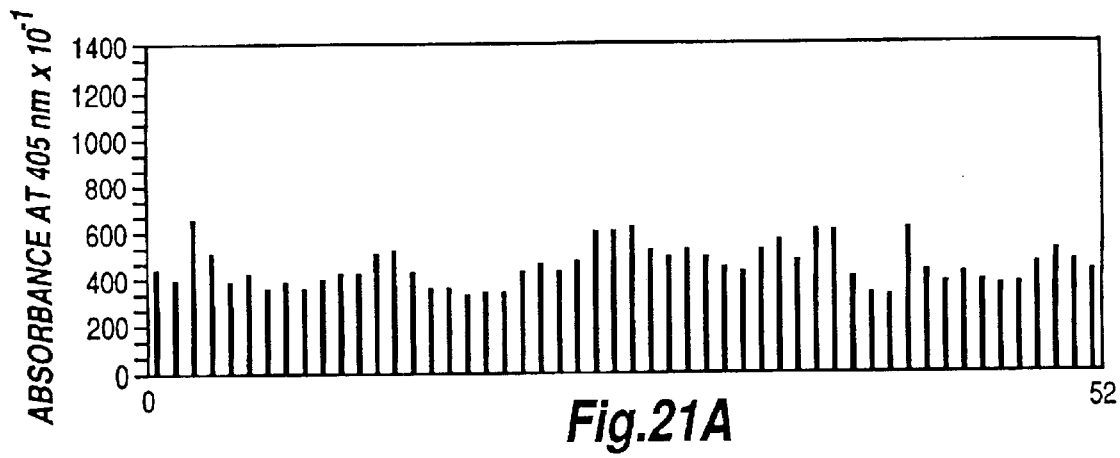
Figure 21B:
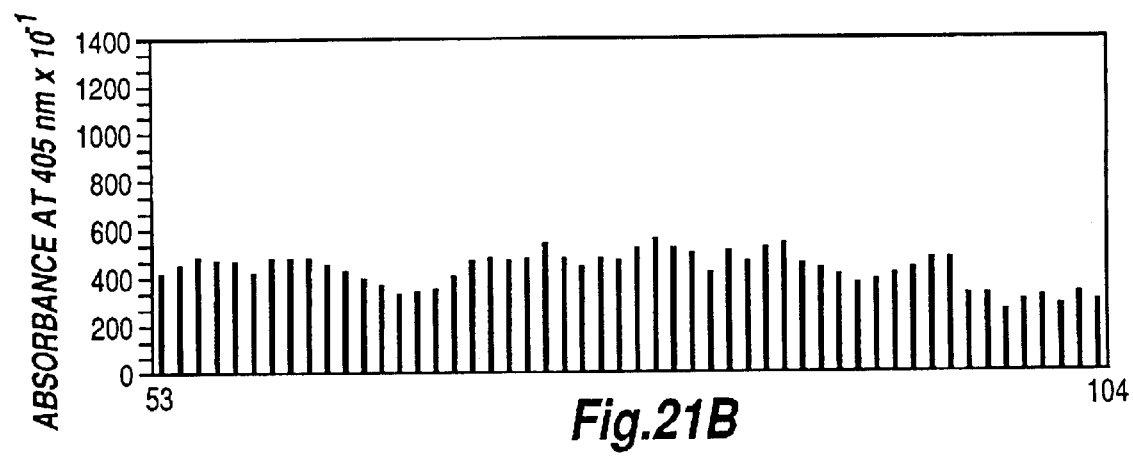
Figure 21C:
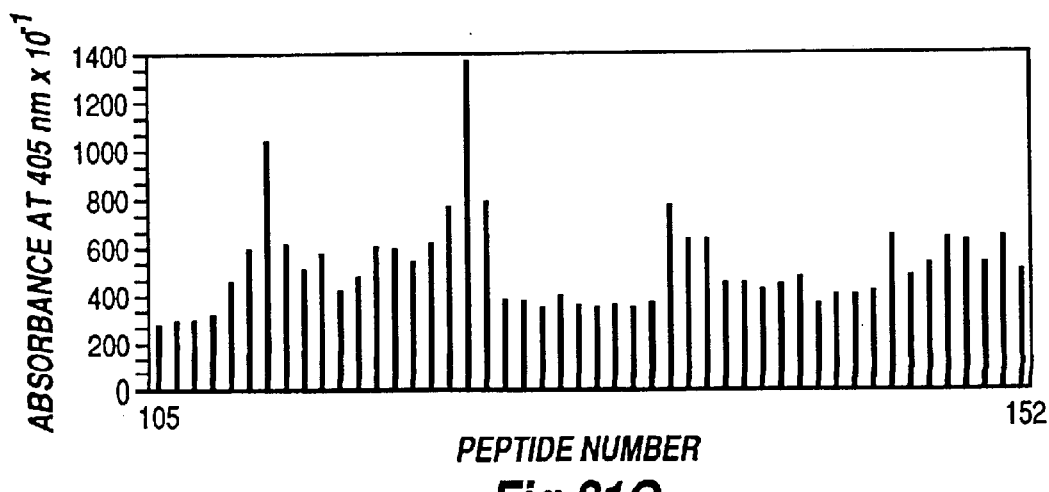
Figure 22:
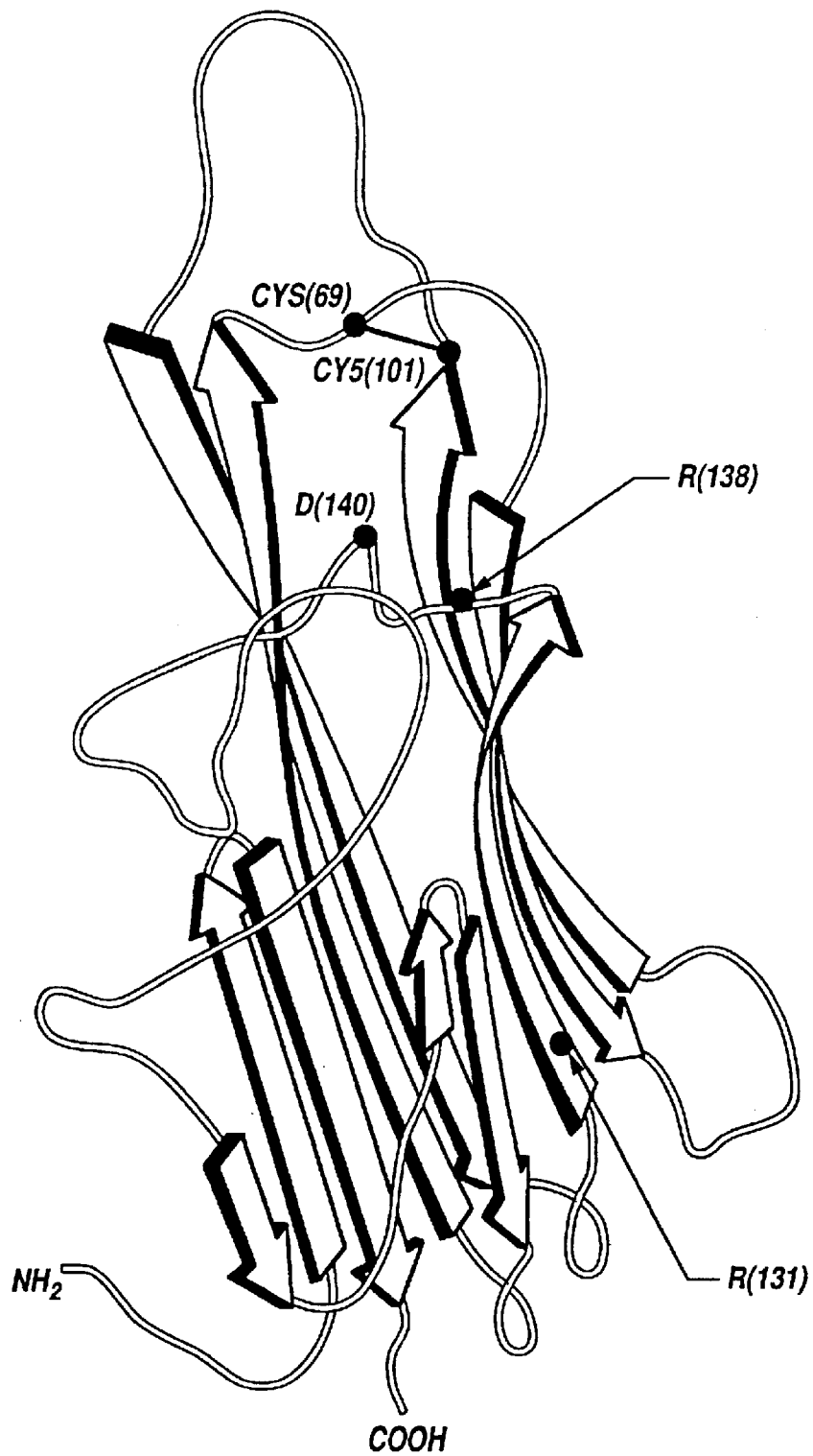

FIGS. 11a and 11b shows the enhancement of TNF-induced tumour regression by MAb 32—dose response at day 1 and day 2;

FIG. 12 shows binding of radio labelled TNF to receptors on bovine aortic endothelial cells;

FIG. 13 shows receptor binding studies of TNF complexed with MAb 32 (—◆—) control antibody (—□—) and MAb 47 (—■—) on melanoma cell line MM418E;

FIG. 14 shows receptor binding studies of TNF complexed with MAb 32 (—◆—) control antibody (—□—) and MAb 47 (—■—) on melanoma cell line IGR3;

FIG. 15 shows receptor binding studies of TNF complexed with MAb 32 (—◆—) control antibody (—□—) and MAb 47 (—■—) on bladder carcinoma cell line 5637;

FIG. 16 shows receptor binding studies of TNF complexed with MAb 32 (—◆—), control antibody (—□—) and MAb 47 (—■—) on breast carcinoma cell line MCF7;

FIG. 17 shows receptor binding studies of TNF complexed with MAb 32 (—◆—) control antibody (—□—) and MAb47 (—■—) on colon carcinoma cell line B10;

FIG. 18 shows the effect on TNF-mediated tumour regression in vivo by MAb 32 (■) control MAb (□) and MAb 47 (*);

FIG. 19 shows the effect on TNF-mediated tumour regression in vivo by control MAb, MAb 32 and univalent FAb' fragments of MAb 32;

FIG. 20 shows the effect on TNF induced tumour regression by control MAb (■), MAb 32 (▨) and peptide 301 antiserum (▨);

FIGS. 21a, 21b and 21c show MAb 32 reactivity with overlapping peptides of 10 AA length; and FIG. 22 shows a schematic three dimensional representation of the TNF molecule.

Figure 23:
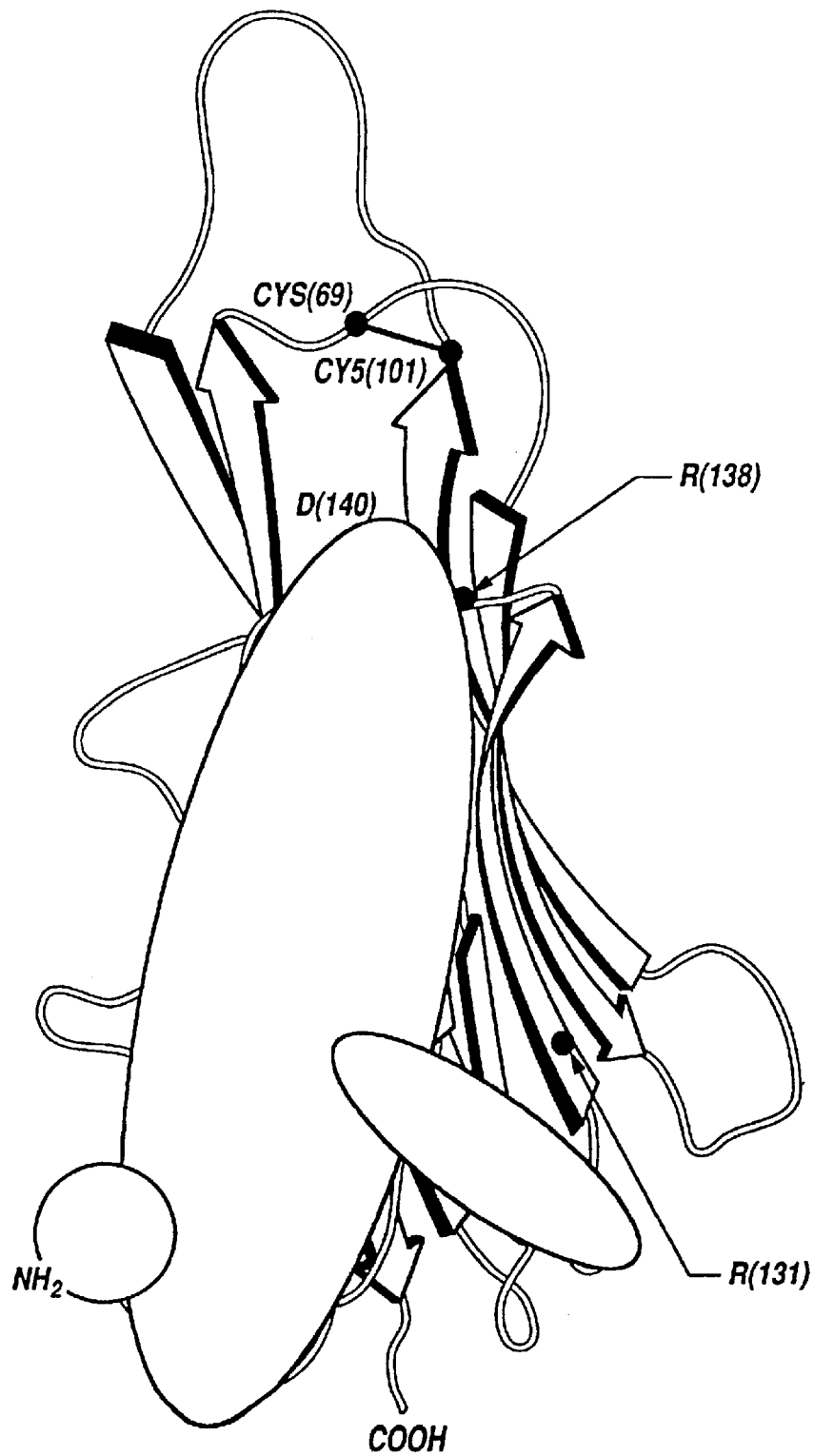
Figure 24:
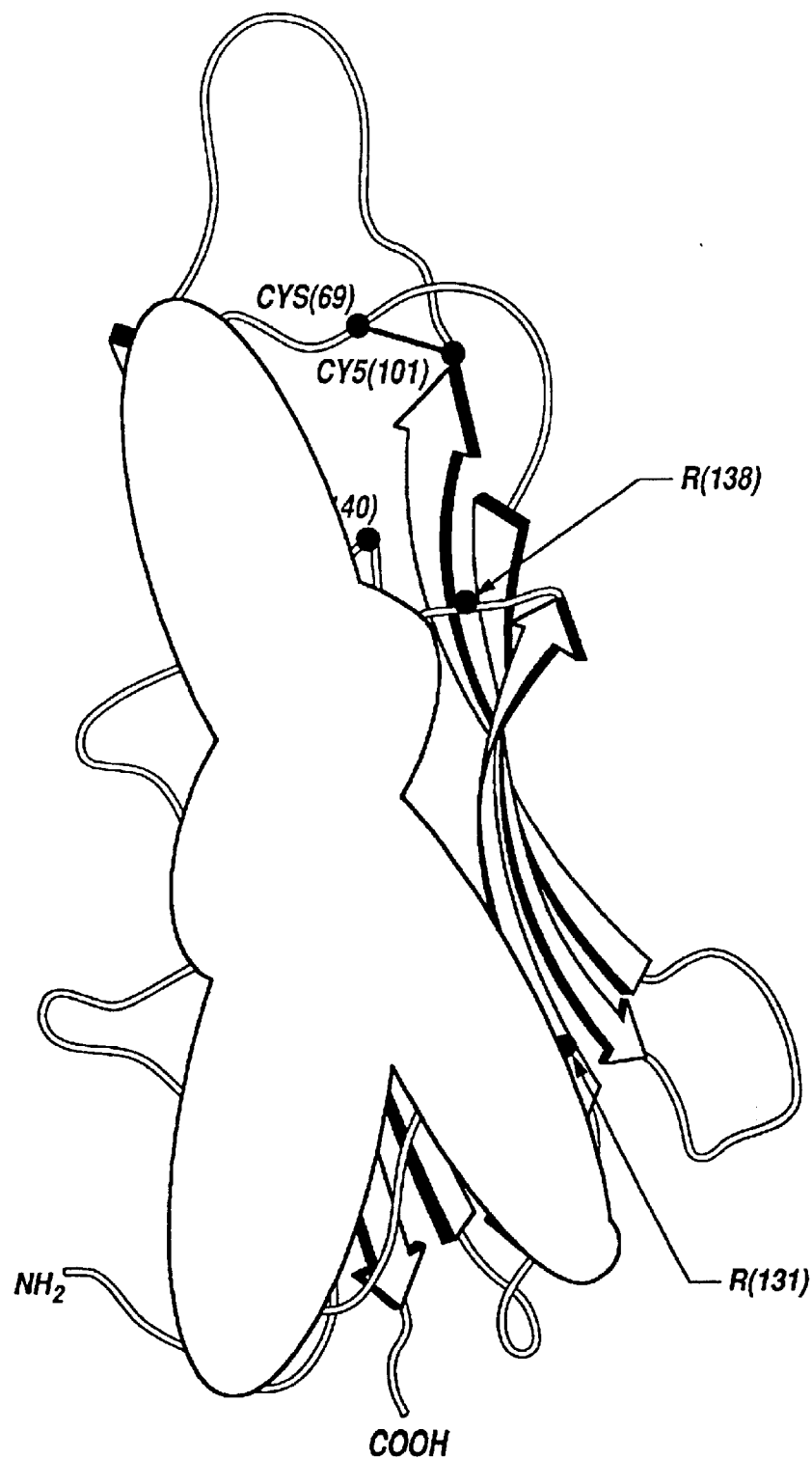
Figure 25:
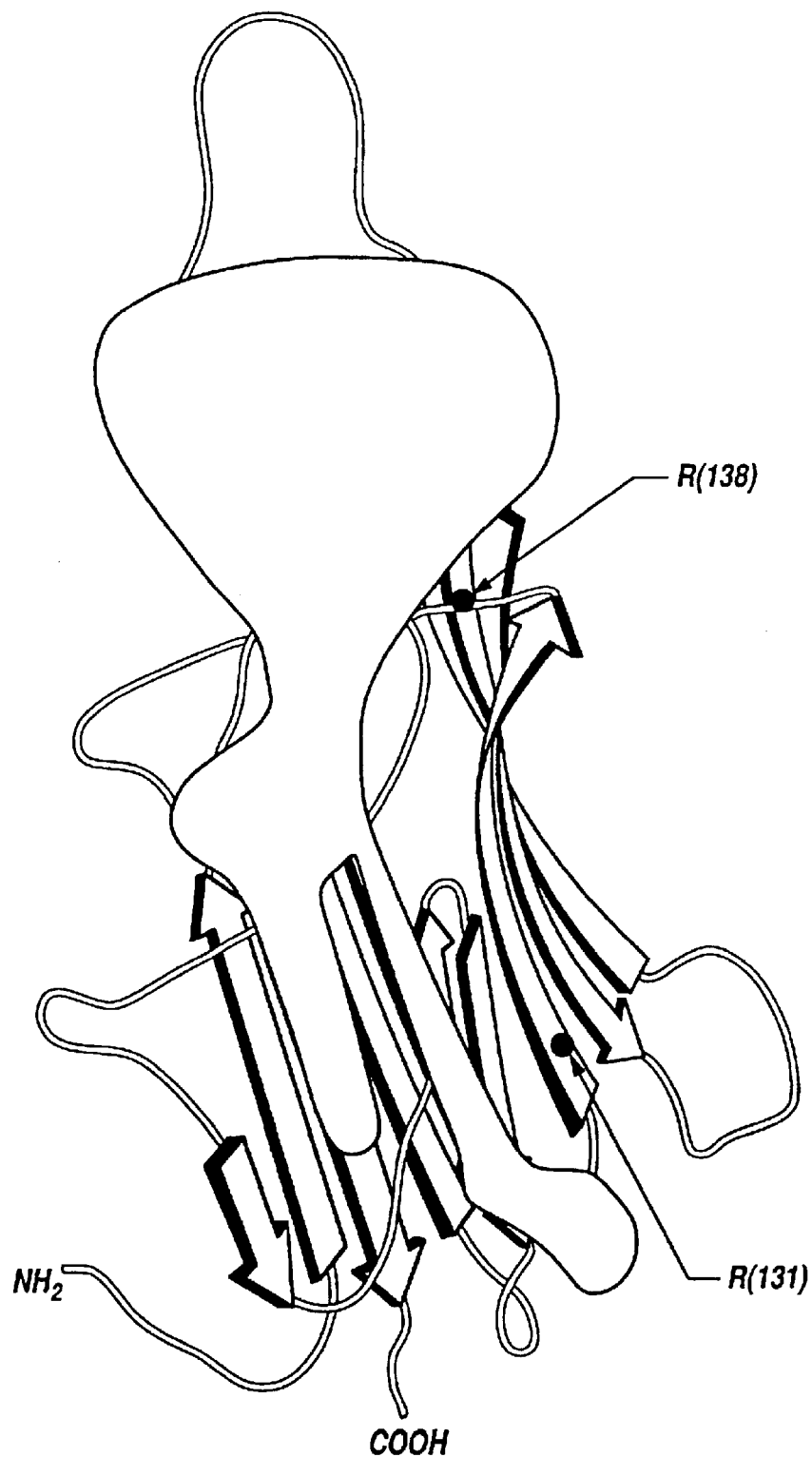
Figure 26:
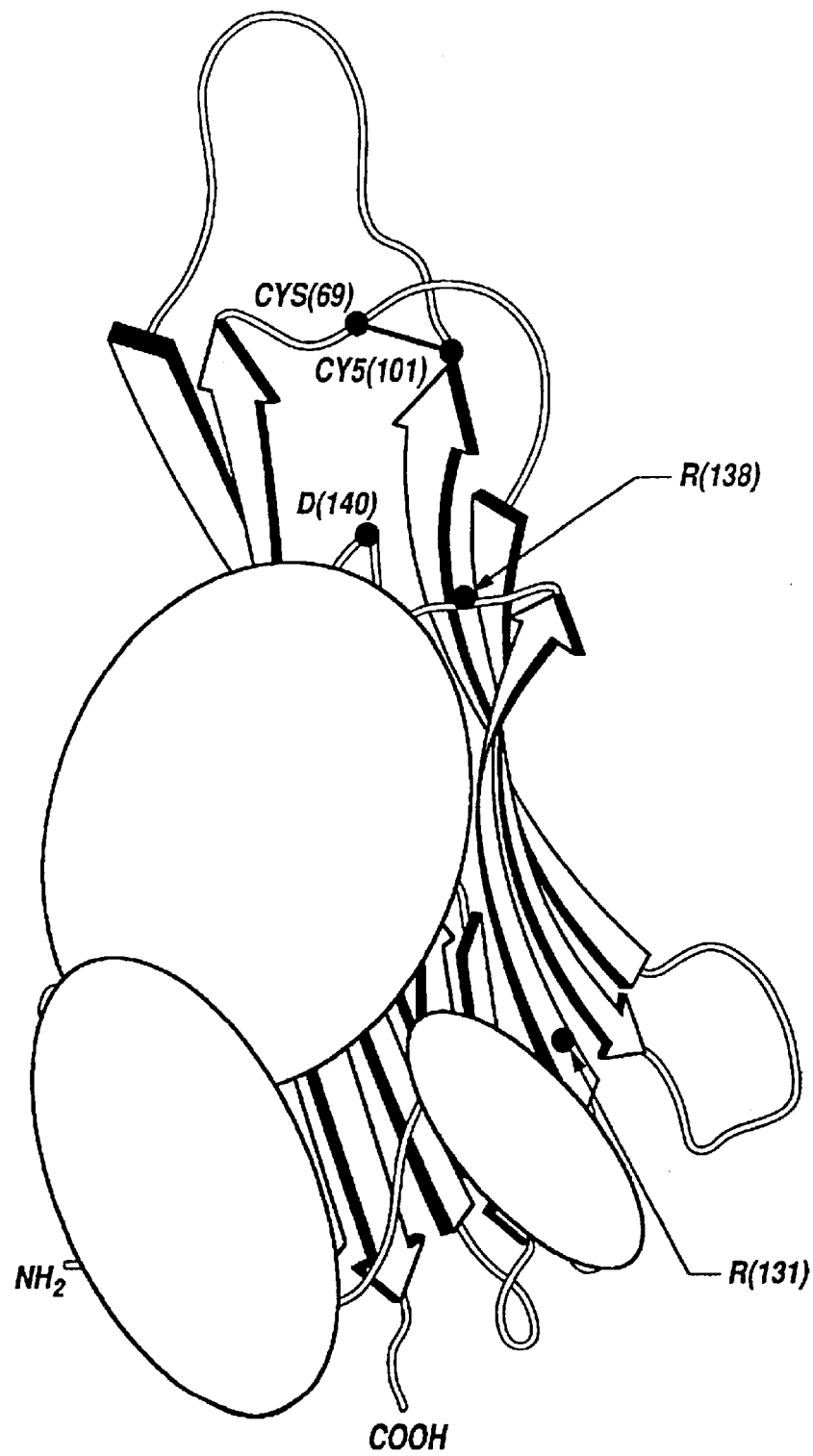
Figure 27:
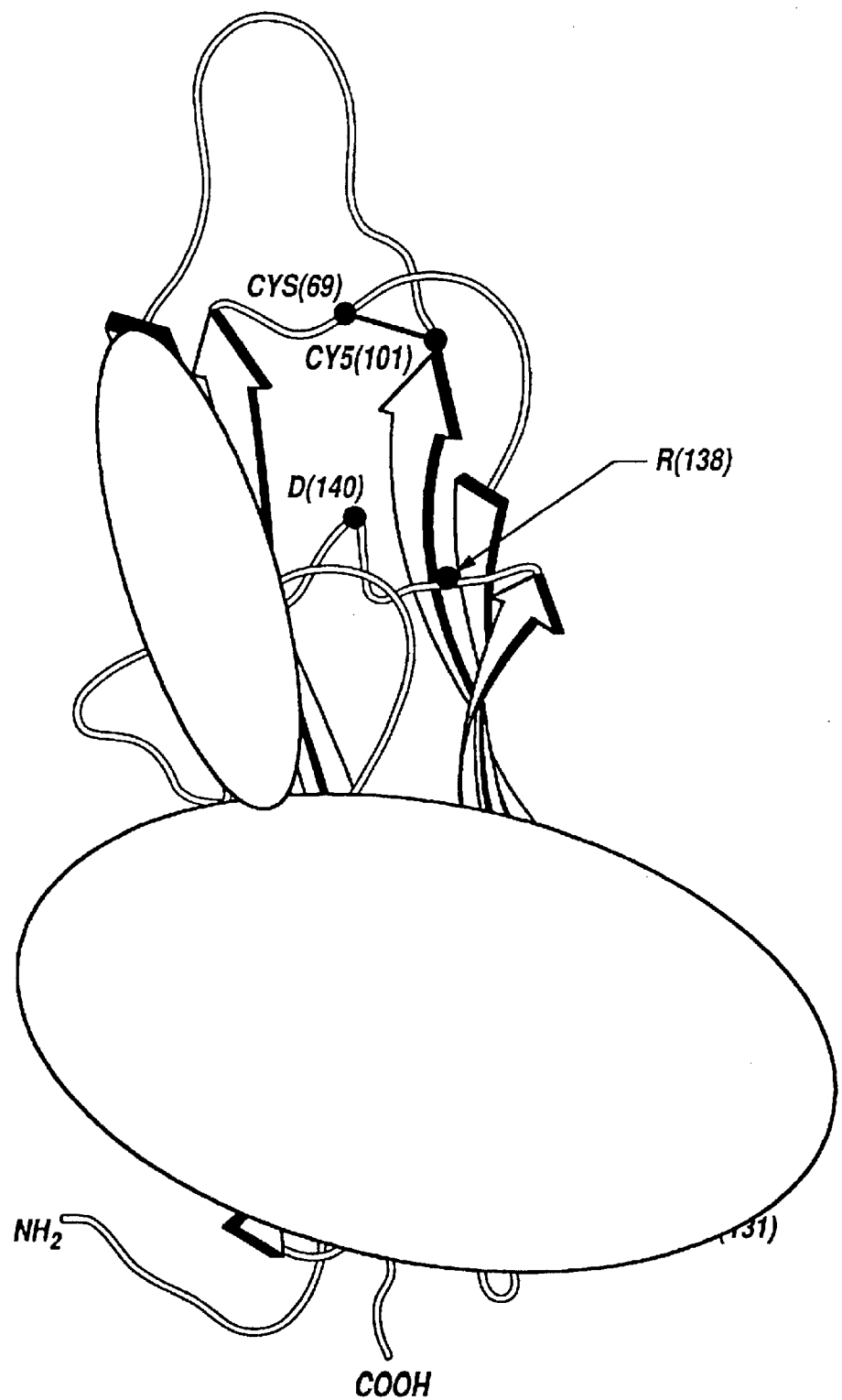
Figure 28:
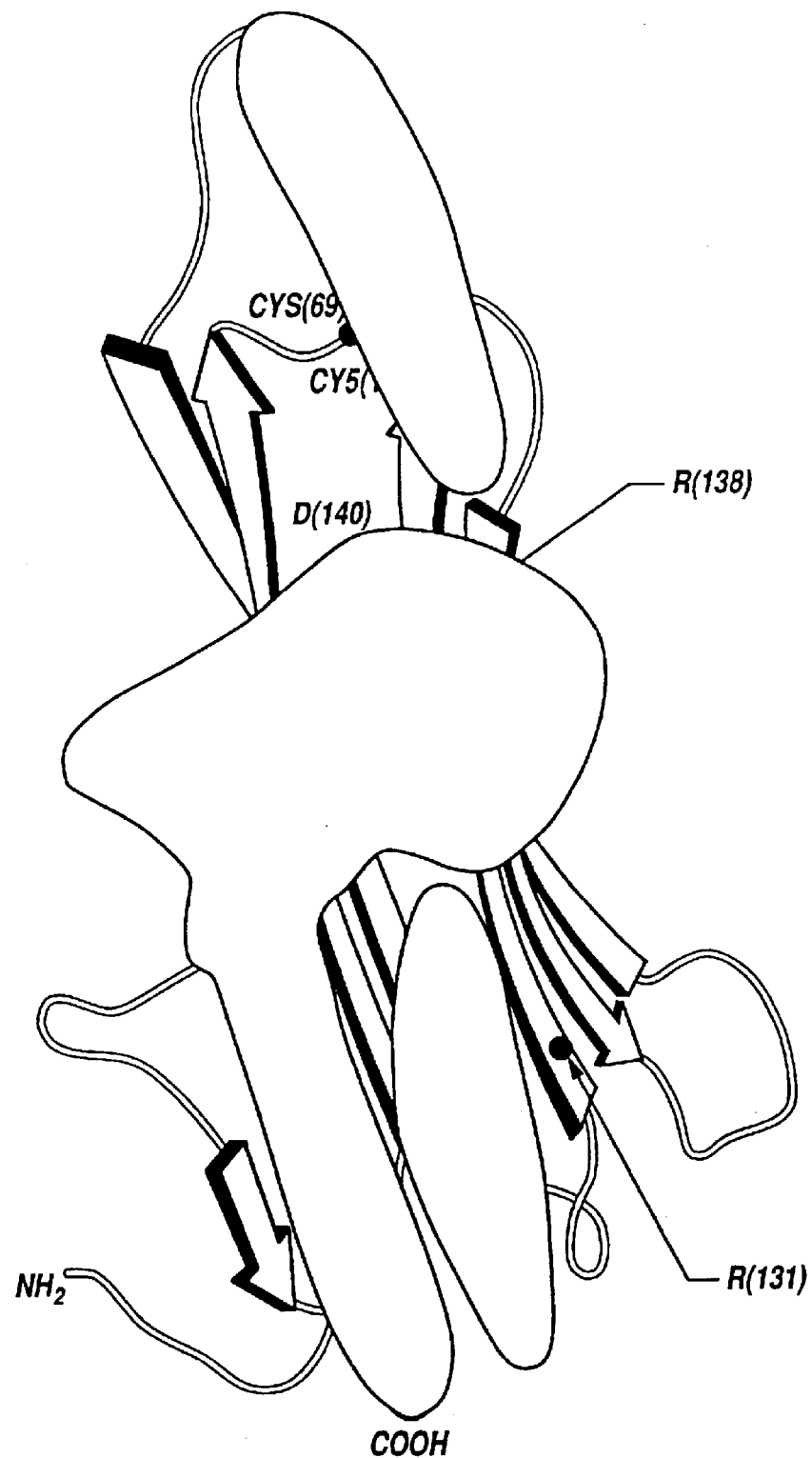
Figure 29:
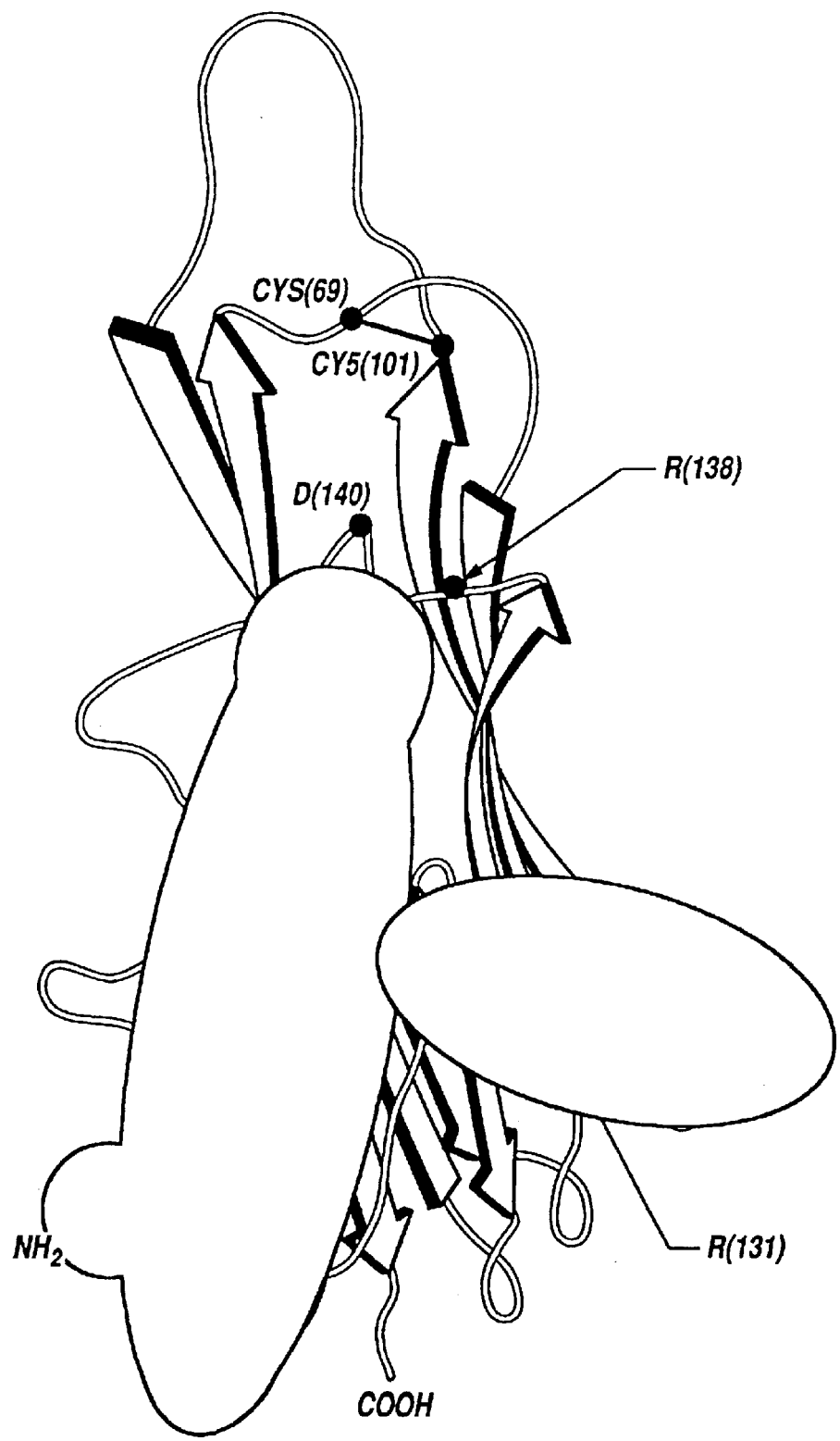
Figure 30:
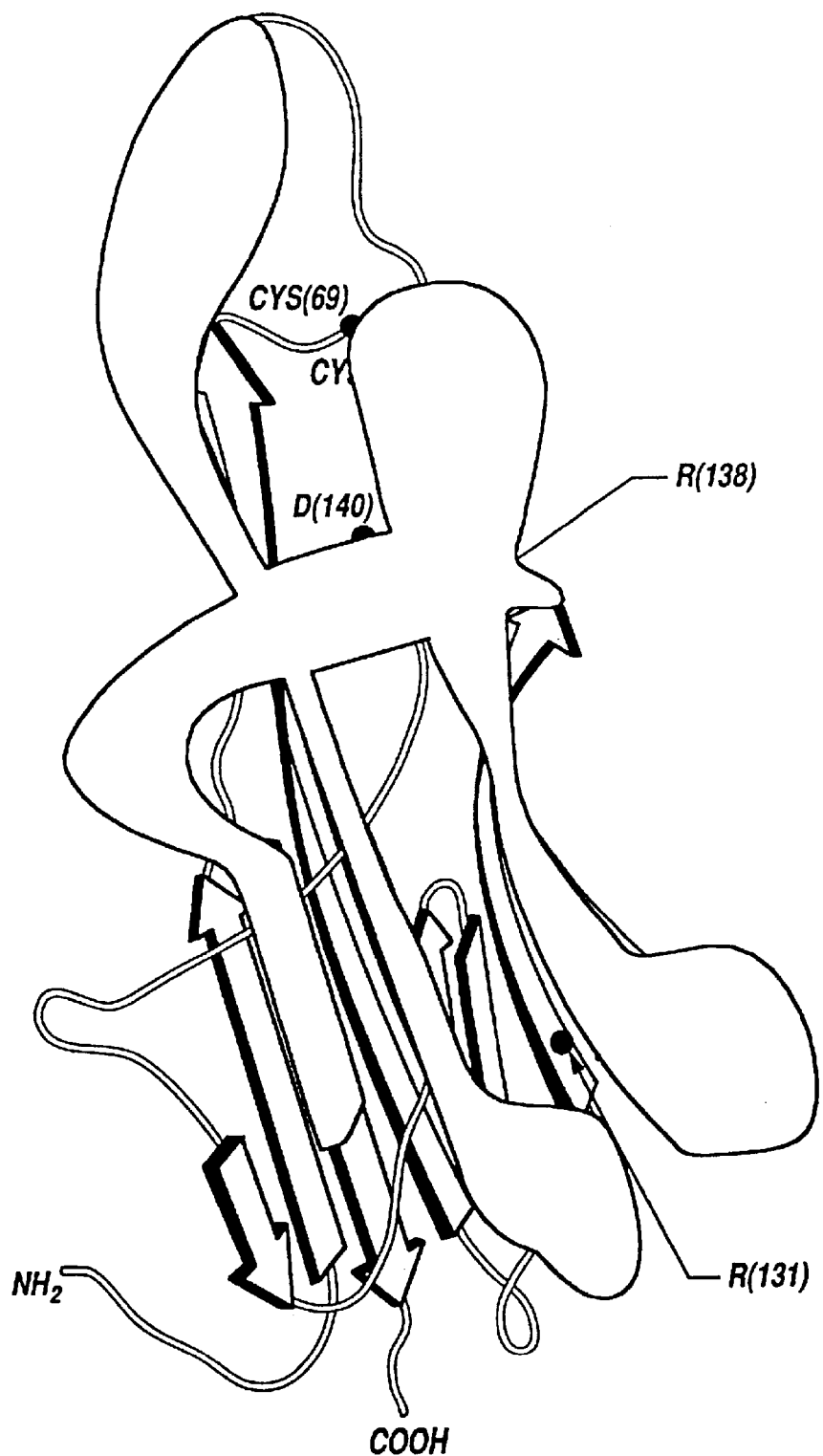
Figure 31:
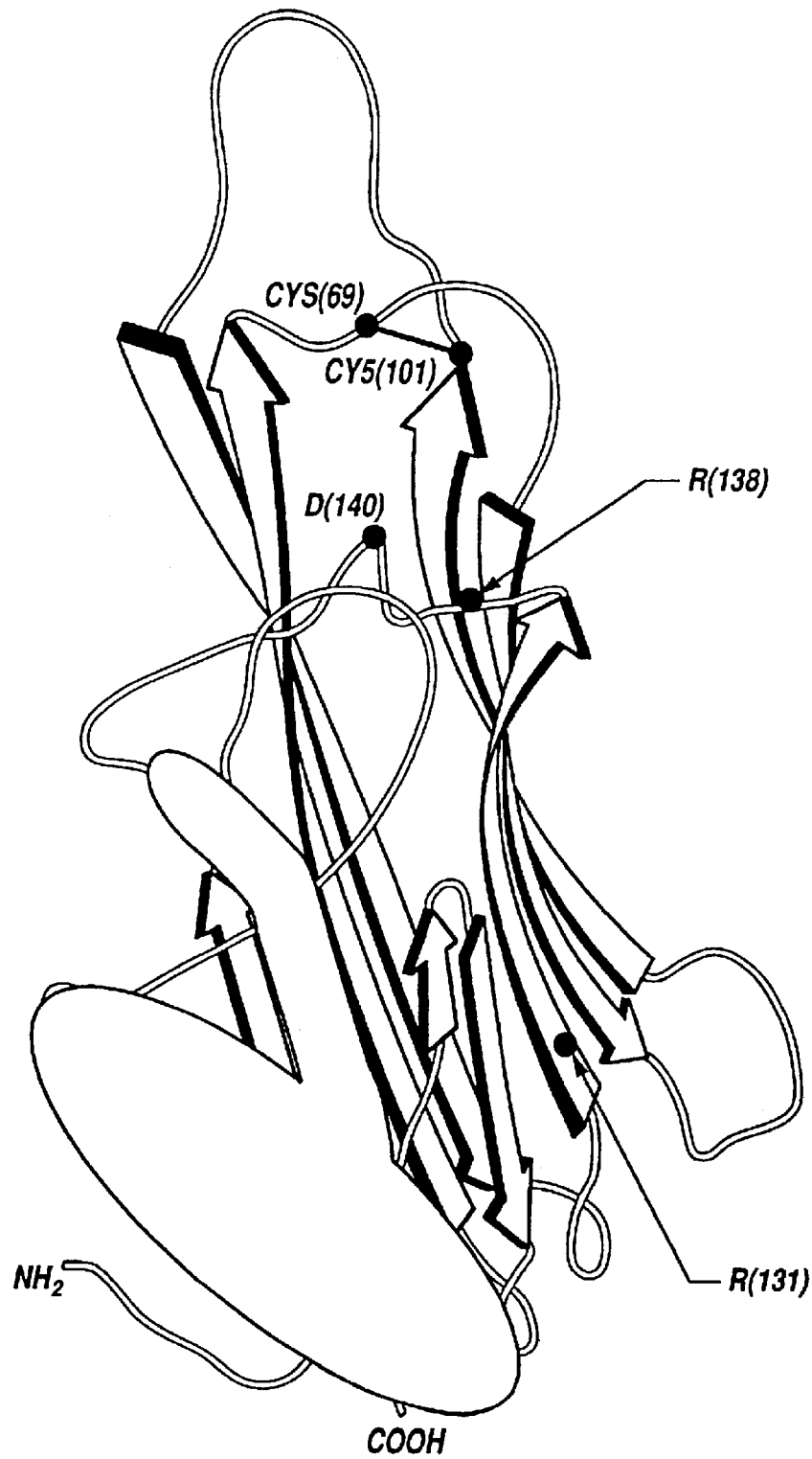
Figure 32:
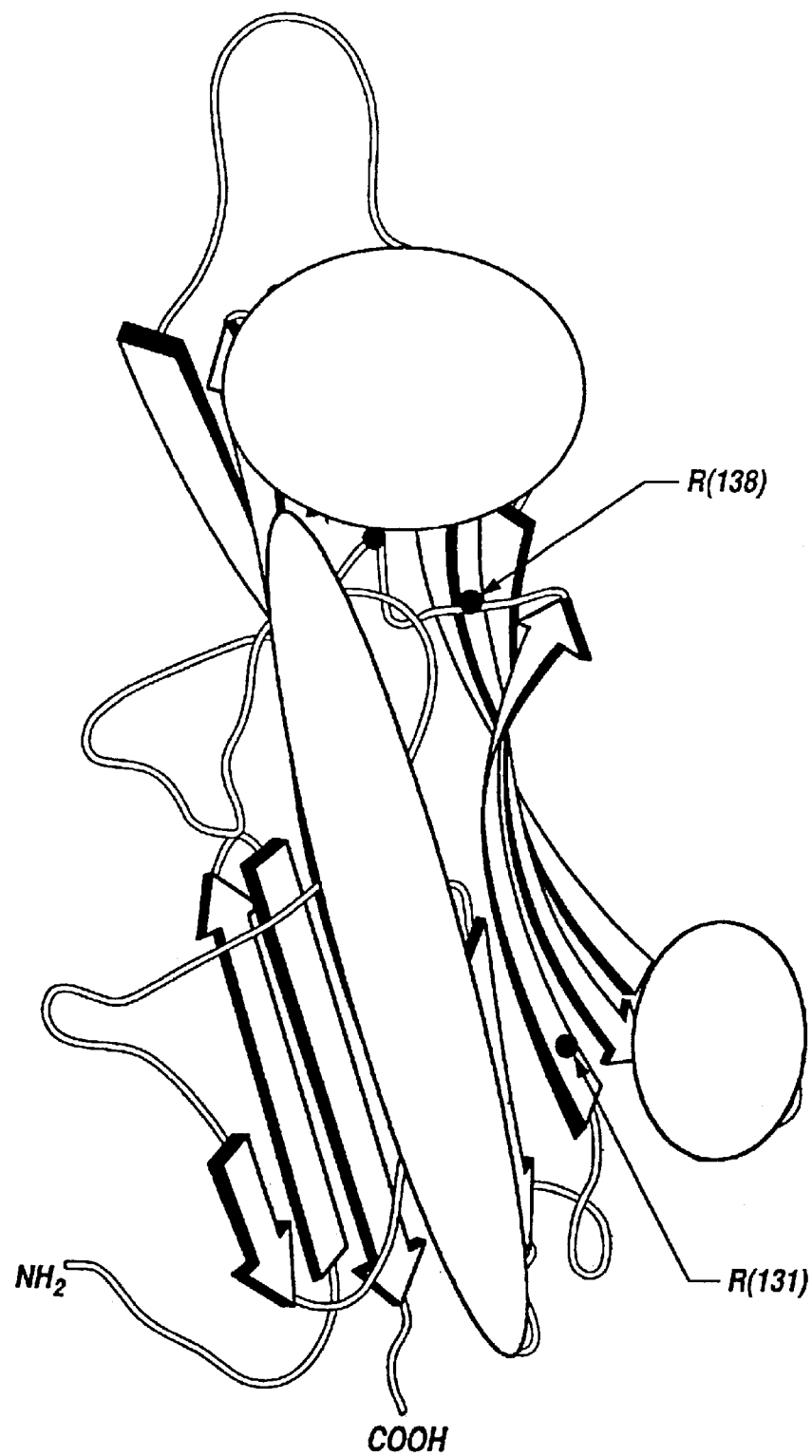
Figure 33:
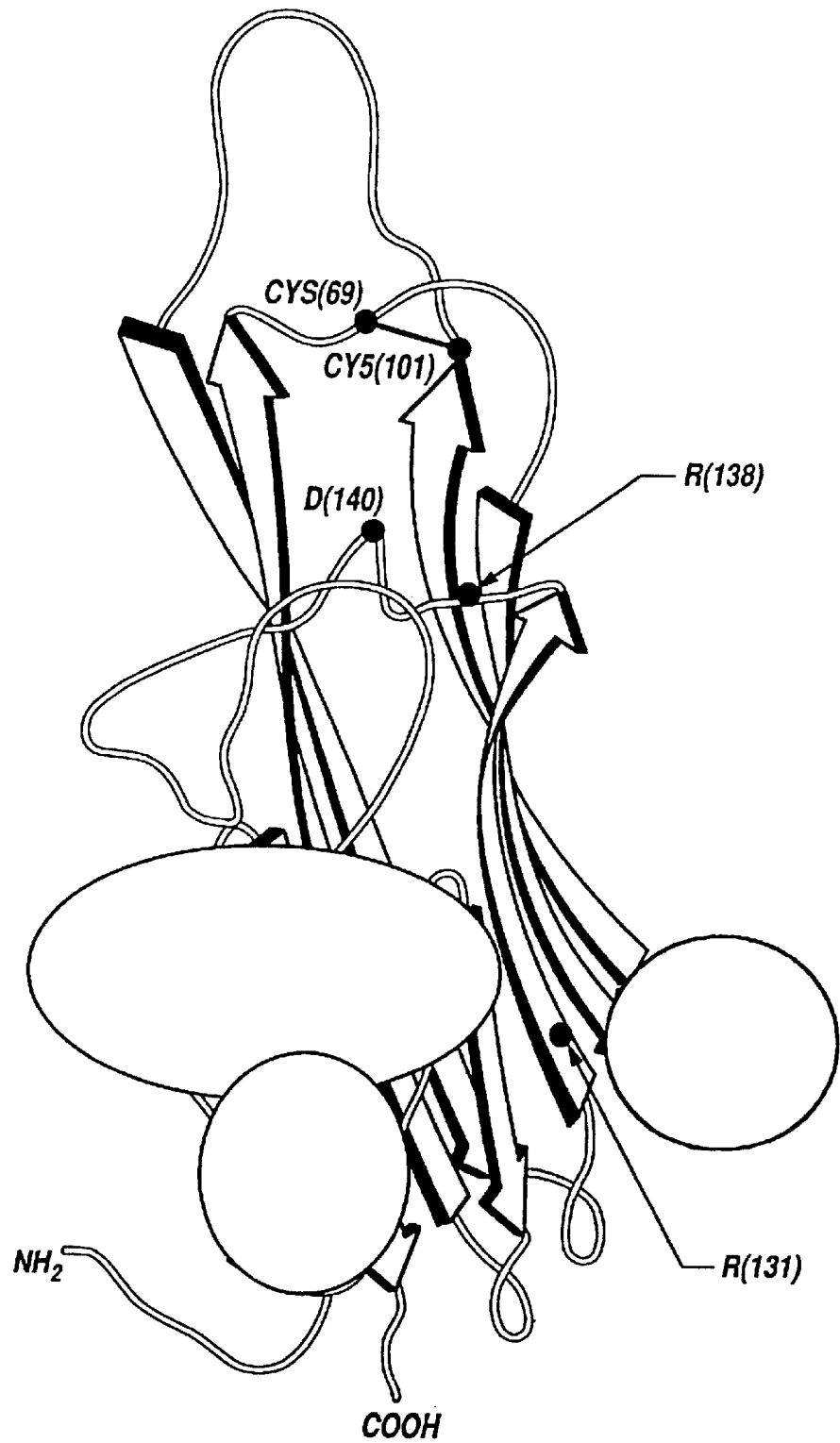
Figure 34:
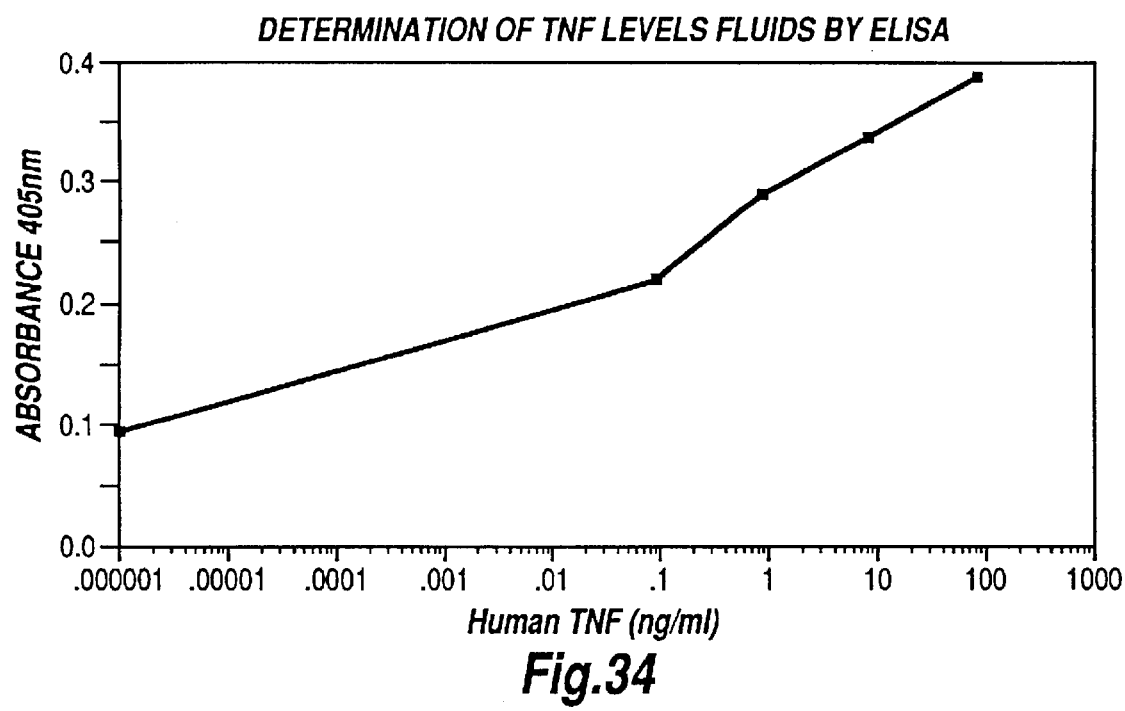

FIG. 23 shows topographically the region of residues 1–20, 56–77, 108–127 and 138–149;

FIG. 24 shows topographically the region of residues 1–18 and 108 –128;

FIG. 25 shows topographically the region of residues 56–79, 110–127 and 136–155;

FIG. 26 shows topographically the region of residues 1–26, 117–128 and 141–153;

FIG. 27 shows topographically the region of residues 22–40, 49–97, 110–127 and 136–153;

FIG. 28 shows topographically the region of residues 12–22, 36–45, 96–105 and 132–157;

FIG. 29 shows topographically the region of residues 1–20 and 76–90;

FIG. 30 shows topographically the region of residues 22–40, 69–97, 105–128 and 135–155;

FIG. 31 shows topographically the region of residues 2–31 and 146–157;

FIG. 32 shows topographically the region of residues 49–98;

FIG. 33 shows topographically the region of residues 22–40 and 70–87;

FIG. 34 shows results of an ELISA using samples containing varying levels of TNF; and FIG. 35 shows the effect of VHP3-VλA2 on anti-tumour activity of TNF.

DESCRIPTION OF THE PREFERRED EMBODIMENTS

Animals and Tumour Cell Lines

In all experiments BALB/C female mice aged 10–12 weeks obtained from the CSIRO animal facility were used. Meth A solid tumour and Meth A ascites tumour cell lines were obtained from the laboratory of Dr. Lloyd J. Old (Sloan Kettering Cancer Centre) and the WEHI-164 fibrosarcoma line was obtained from Dr. Geeta Chauhdri (John Curtin School of Medical Research, Australian National University).

Fusions and Production of Hybridomas

Mice were immunised with 10 ug human recombinant TNF intra-peritoneally in Freund's complete adjuvant. One month later 10 ug TNF in Freund's incomplete adjuvant was administered. Six weeks later and four days prior to fusion selected mice were boosted with 10 ug TNF in PBS. Spleen cells from immune mice were fused with the myeloma Sp2/0 according to the procedure of Rathjen and Underwood (1986, Mol. Immunol. 23, 441). Cell lines found to secrete anti-TNF antibodies by radioimmunoassay were subcloned by limiting dilution on a feeder layer of mouse peritoneal macrophages. Antibody subclasses were determined by ELISA (Misotest, Commonwealth Serum Laboratories).

Radioimmunoassay

TNF was iodinated using lactoperoxidase according to standard procedures. Culture supernatants from hybridomas (50 ul) were incubated with 125I TNF (20,000 cpm in 50 ul) overnight at 4° C. before the addition of 100 ul Sac-Cel (donkey anti-mouse/rat immunoglobulins coated cellulose, Wellcome Diagnostics) and incubated for a further 20 minutes at room temperature (20° C.). Following this incubation 1 ml of PBS was added and the tubes centrifuged at 2,500 rpm for 5 minutes. The supernatant was decanted and the pellet counted for bound radioactivity.

Antibody-Antibody Competition Assays

The comparative specificites of the monoclonal antibodies were determined in competition assays using either immobilized antigen (LACT) or antibody (PACT) (Aston and Ivanyi, 1985, Pharmac. Therapeut. 27, 403).
PACT Flexible microtitre trays were coated with monoclonal antibody (sodium sulphate precipitated globulins from mouse ascites fluid, 100 micrograms per ml in sodium bicarbonate buffer, 0.05M, pH 9.6) overnight at 4° C. prior to blocking non-specific binding sites with 1% bovine serum albumin in PBS (BSA/PBS). The binding of 125I TNF to immobilised antibody was determined in the presence of varying concentrations of a second anti-TNF monoclonal antibody. Antibody and TNF were added simultaneously and incubated for 24 hours prior to washing with PBS (4 times) and counting wells for bound radioactivity. 100% binding was determined in the absence of heterologous monoclonal antibody while 100% competition was determined in the presence of excess homologous monoclonal antibody. All dilutions were prepared in BSA/PBS.

LACT

The binding of protein A purified, radiolabelled monoclonal antibodies to TNF coated microtitre wells was determined in the presence of varying concentrations of a second monoclonal antibody. Microtitre plates were coated with TNF (50 micrograms per ml) as described above. Quantities of competing antibodies (50 microliters) were pre-incubated on plates for 4 hour at 4° C. prior to addition of 125I monoclonal antibody (30,000 cpm) for a further 24 hours. Binding of counts to wells was determined after four washes with PBS. 100% binding was determined in the absence of competing antibody while 100% competition was determined in the presence of excess unlabelled monoclonal antibody.

WEHI-164 Cytotoxicity Assay

Bioassay of recombinant TNF activity was performed according to Espevik and Nissen-Meyer (1986, J. Immunol. Methods 95, 99). The effect of the monoclonal antibody on TNF activity was determined by the addition of the monoclonal antibody to cell cultures at ABT90.

Tumour Regression Experiments

Modulation of TNF-induced tumour regression activity by monoclonal antibodies was assessed in three tumour models: the subcutaneous tumours WEHI-164 and Meth A sarcoma and the ascitic Meth A tumour. Subcutaneous tumours were induced by the injection of approximately $5 \times 10^5$ cells. This produced tumours of between 10–15 mm approximately 14 days later. Mice were injected intra-peritoneally with human recombinant TNF (10 micrograms) plus monoclonal antibody (200 microliters ascites globulin) for four consecutive days. Control groups received injections of PBS alone or TNF plus monoclonal antibody against bovine growth hormone. At the commencement of each experiment tumour size was measured with calipers in the case of solid tumours or tumour-bearing animals weighed in the case of ascites mice. These measurements were taken daily throughout the course of the experiment.

Radio-Receptor Assays

WEHI-164 cells grown to confluency were scrape harvested and washed once with 1% BSA in Hank's balanced salt solution (HBSS, Gibco). 100 ul of unlabelled TNF (1–10,000 ng/tube) or monoclonal antibody (10 fold dilutions commencing 1 in 10 to 1 in 100,000 of ascitic globulin) wasadded to 50 ul 125I TNF (50,000 cpm). WEHI cells were then added (200 microliters containing $2 \times 10^6$ cells). This mixture was incubated in a shaking water bath at 37° C. for 3 hours. At the completion of this incubation 1 ml of HBSS was added and the cells spun at 16,000 rpm for 30 seconds. The supernatant was discarded s and bound 125I TNF in the cell pellet counted. All dilutions were prepared in HBSS containing 1% BSA.

Procoagulant Induction by TNF on Endothelial Cells

Bovine aortic endothelial cells (passage 10) were grown in RPMI-1640 containing 10% foetal calf serum (FCS), penicillin, streptomycin, and 2-mercaptoethanol at 37° C. in 5% $CO_2$. For induction of procoagulant activity by TNF the cells were trypsinised and plated into 24-well Costar trays according to the protocol of Bevilacqua et al., 1986 (PNAS 83, 4533). TNF (0–500 units/culture) and monoclonal antibody (1 in 250 dilution of ascitic globulin) was added after washing of the confluent cell monolayer with HBSS. After 4 hours the cells were scrape harvested, frozen and sonicated. Total cellular procoagulant activity was determined by the recalcification time of normal donor platelet-poor plasma performed at 37° C., 100 microliters of citrated platelet-poor plasma was added to 100 ul of cell lysate and 100 ul of calcium chloride (30 mM) and the time taken for clot formation recorded. In some experiments tumour cell culture supernatant was added to endothelial cells treated with TNF and/or monoclonal antibody (final concentration of 1 in 2).

Incorporation of 125I Fibrinogen into Tumours of Mice Treated with TNF and Monoclonal Antibody In order to examine the effect of TNF and monoclonal antibodies on fibrin formation in vivo, BALB/c mice were injected subcutaneously with WEHI-164 cells ($10^5$ cells/animal). After 7–14 days, when tumours reached a size of approximately 1 cm in diameter, animals were injected intra-peritoneally with TNF (10 ug/animal) and 125I human fibrinogen (7.5 ug/animal, 122 uCi/mg Amersham) either alone or in the presence of monoclonal antibody to human TNF (200 ul/animal ascitic globulin). Monoclonal antibody against bovine growth hormone,was used as control monoclonal antibody. Two hours after TNF infusion incorporation of 125I fibrinogen into mouse tissue was determined by removing a piece of tissue, weighing it and counting the sample in a gamma counter.

In all 13 monoclonal antibodies reacting with human TNF were isolated. These monoclonal antibodies were designated MAb 1, MAb 11, MAb 12, MAb 20, MAb 21, MAb 25, MAb 31, MAb 32, MAb 37, MAb 42, MAb 47, MAb 53 and MAb 54. The effect of these monoclonal antibodies on the bioactivity of human TNF is set out in Table 2.

As can be seen from Table 2, whilst some monoclonal antibodies inhibit both anti-tumour activity and activation of coagulation by human TNF (MAb 1, 47 and 54) not all antibodies which inhibit the anti-tumour activity inhibit activation of coagulation either in vitro or in viva (MAb 11, 12, 25 and 53). Indeed MAb 21 which inhibited tumour regression enhanced the activation of coagulation in vivo.

TABLE 2

EFFECT OF MONOCLONAL ANTIBODIES ON TNF BIOACTIVITY

| TNF BIOACTIVITY | MONOCLONAL ANTIBODY | | | | | | | | | | | | |
|---|---|---|---|---|---|---|---|---|---|---|---|---|---|
| | 1 | 11 | 12 | 20 | 21 | 25 | 31 | 32 | 37 | 42 | 47 | 53 | 54 |
| Cytotoxicity | − | − | − | 0 | − | − | 0 | 0 | 0 | 0 | − | − | − |
| Tumour Regression | − | − | − | 0 | − | − | 0 | + | 0 | 0 | − | − | − |

TABLE 2-continued

EFFECT OF MONOCLONAL ANTIBODIES ON TNF BIOACTIVITY

| TNF BIOACTIVITY | MONOCLONAL ANTIBODY | | | | | | | | | | | |
|---|---|---|---|---|---|---|---|---|---|---|---|---|
| | 1 | 11 | 12 | 20 | 21 | 25 | 31 | 32 | 37 | 42 | 47 | 53 | 54 |
| Induction of Procoagulant (Endothelial | – | 0 | 0 | – | – | 0 | 0 | – | 0 | – | – | – | – |
| Fibrin Deposition (tumour) | – | – | – | + | + | + | + | + | 0 | – | – | 0 | – |
| Receptor Binding (WEHI - 164) | – | – | – | 0 | – | – | 0 | +/0* | 0 | 0 | – | – | – |

+ Enhancement
0 No effect
– Inhibition
*Depending on MAb concentration in the case of WEHI-164 tumour cells and tumour type (see FIGS. 3, 13–17).

MAbs 1, 47 and 54, which have been shown in competition binding studies to share an epitope on TNF, can be seen to have highly desirable characteristics in treatment of toxic shock and other conditions of bacterial, viral and parasitic infection where TNF levels are high requiring complete neutralisation of TNF. Other monoclonal antibodies such as MAb 32 are more appropriate as agents for coadministration with TNF during cancer therapy since they do not inhibit tumour regression but do inhibit activation of coagulation. This form of therapy is particularly indicated in conjunction with cytotoxic drugs used in cancer therapy which may potentiate activation of coagulation by TNF (e.g. vinblastin, acyclovir, IFN alpha, IL-2, actinomycin D, AZT, radiotherapy, adriamycin, mytomycin C, cytosine arabinoside, dounorubicin, cis-platin, vincristine, 5-flurouracil, bleomycin, (Watanabe N et al 1988 Immunopharmacol. Immunotoxicol. 10 117–127) or in diseases where at certain stages TNF levels are low (e.g. AIDS) and where individuals may have AIDS associated cancer e.g. Kaposi sarcoma, non-Hodgkins lymphoma and squamous cell carcinoma.

Figure 1:
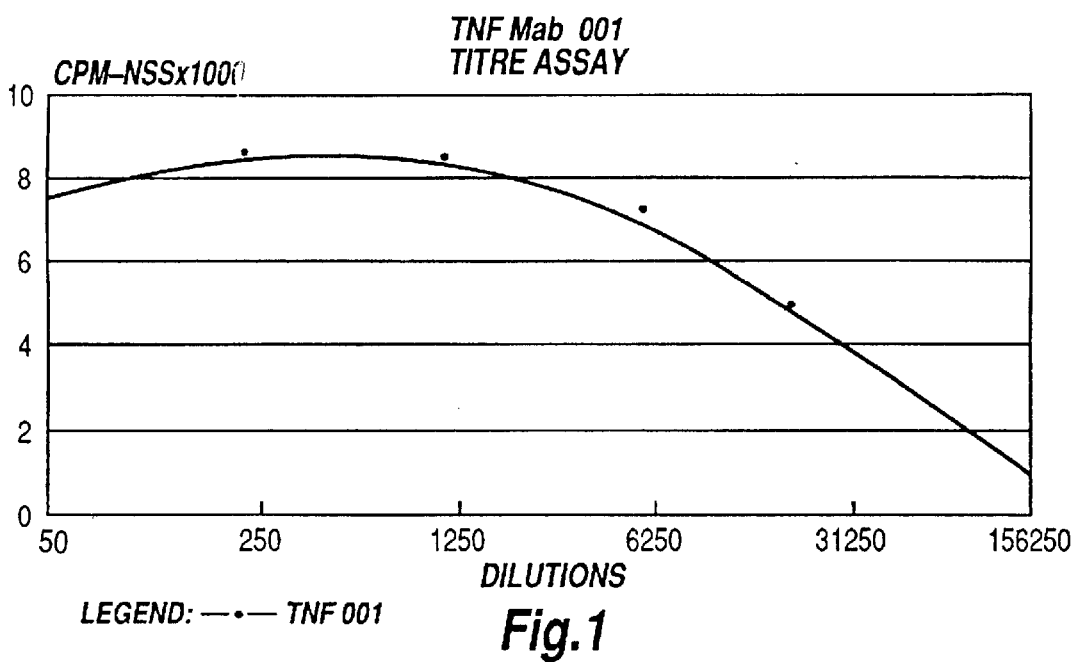

Monoclonal antibody MAb 1 has been found to have the following characteristics:

1. Binds human recombinant TNF alpha, butnohua lymphotoxin (TNF beta) or human interferon. Similarly MAb 1 does not cross-react with recombinant murine TNF (FIG. 1).

Figure 2:
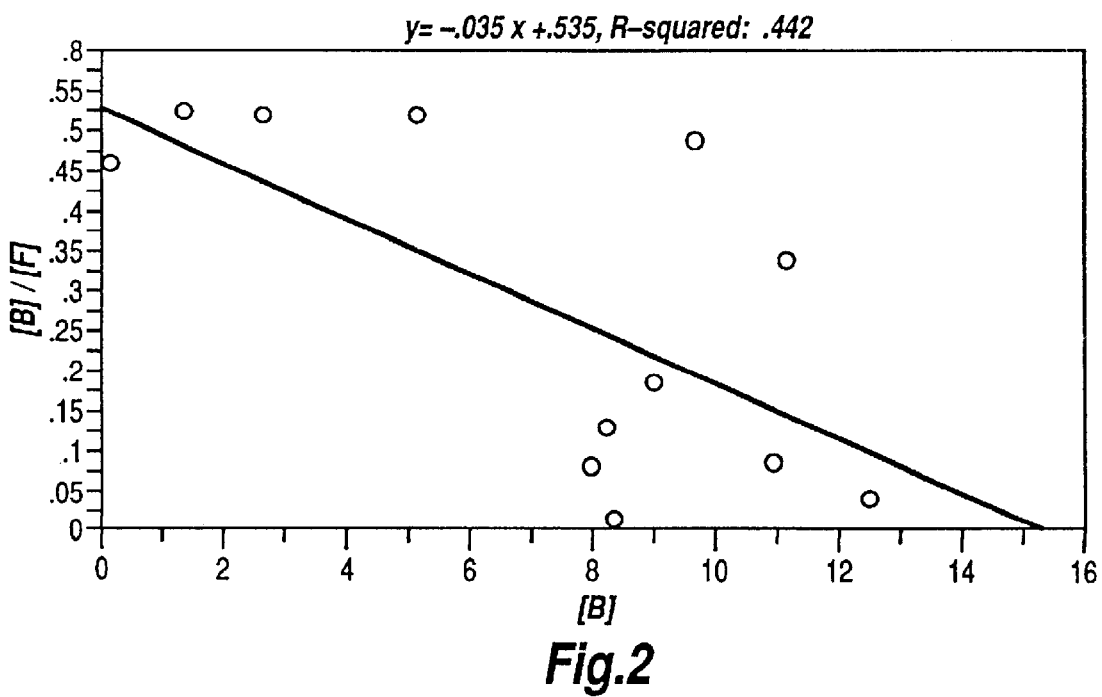

2. MAb 1 is of the immunoglobulin type IgG1, K with an apparent affinity of $4.4 \times 10^9$ moles/liter (FIG. 2).

Figure 3:
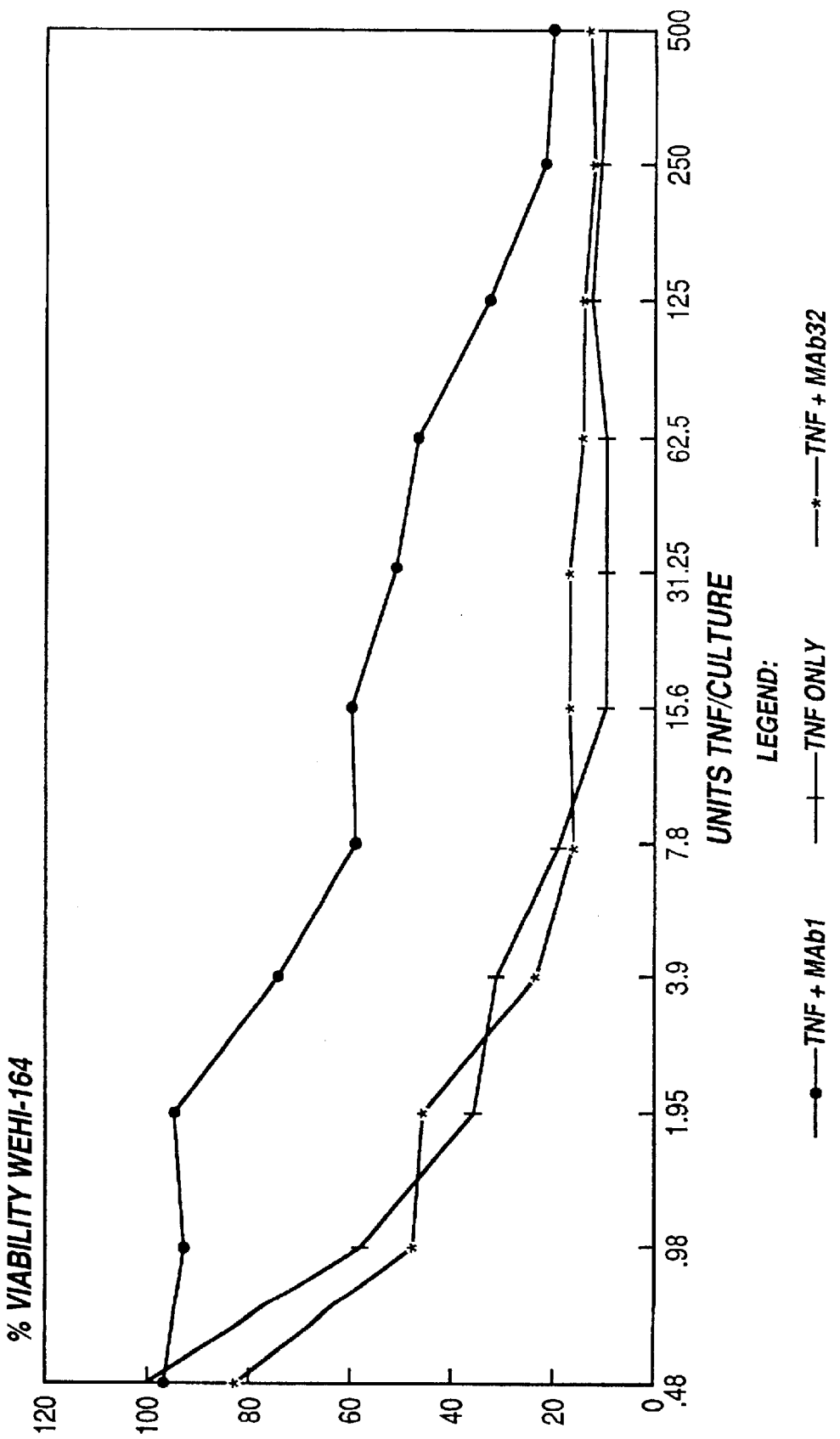
FIG. 3 shows the effect of anti-TNF monoclonal antibodies 1 and 32 on TNF cytotoxicity in WEHI-164 cells.

3. MAb neutralises the cytotoxic effect of recombinant human TNF on WEHI-164 mouse fibrosarcoma cells in culture. One microgram of MAb 1 neutralizes approximately 156.25 units of TNF In vitro (FIG. 3).

Figure 4:
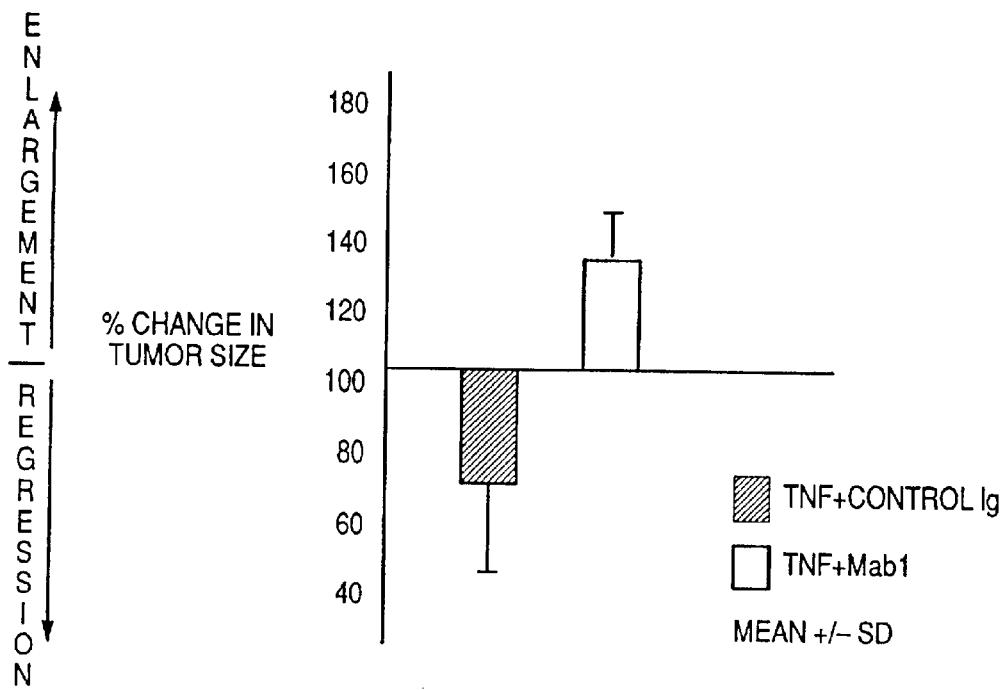
FIG. 4 shows the effect of MAb 1 on TNF-induced regression of a Meth A solid tumour.
Figure 5:
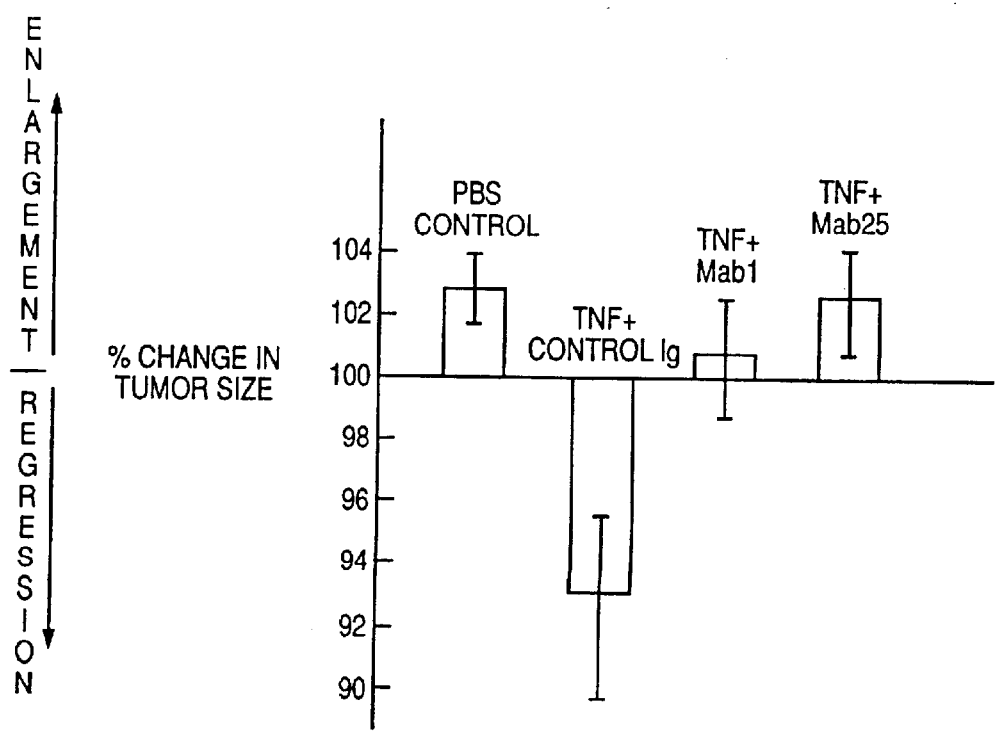
FIG. 5 shows the effect of MAbs 1 and 25 on TNF-induced Meth A Ascites tumour regression.
Figure 9:
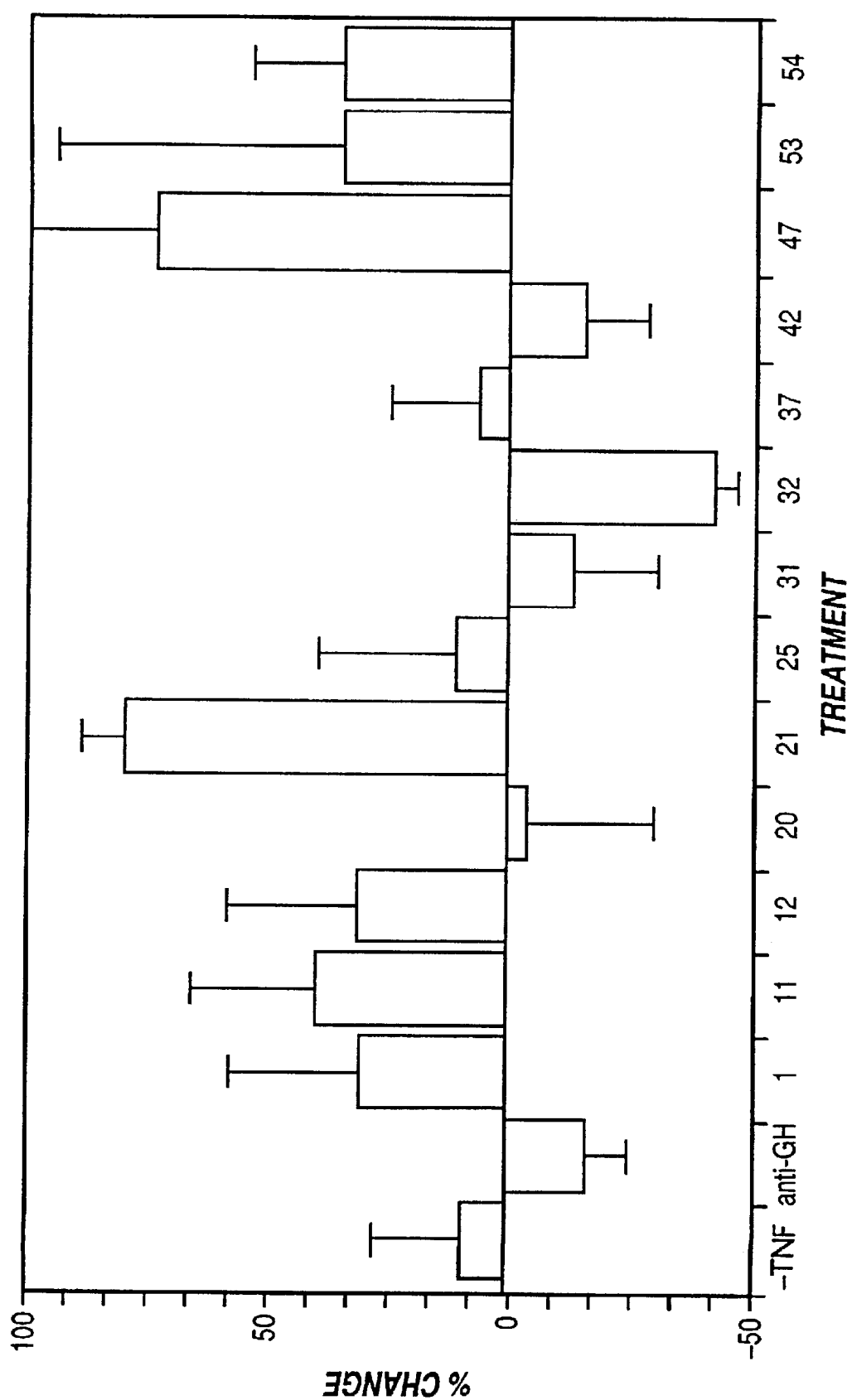
FIG. 9 shows the effect of anti-TNF MAbs on TNF-induced regression of WEHI-164 tumours.

4. MAb 1 neutralises the tumour regression activity of TNF in the following mouse tumour models in vivo; WEHI-164 subcutaneous solid, tumour, the Meth A subcutaneous solid tumour and the Meth A ascites tumour (FIGS. 4, 5 and 9).

5. Mab1 prevents cerebral damage caused by human TNF in mice infected with malarial parasites.

6. In radioreceptor assays MAb 1 prevents binding of TNF to receptors on WEHI-164 cells (Table 3).

Figure 6:
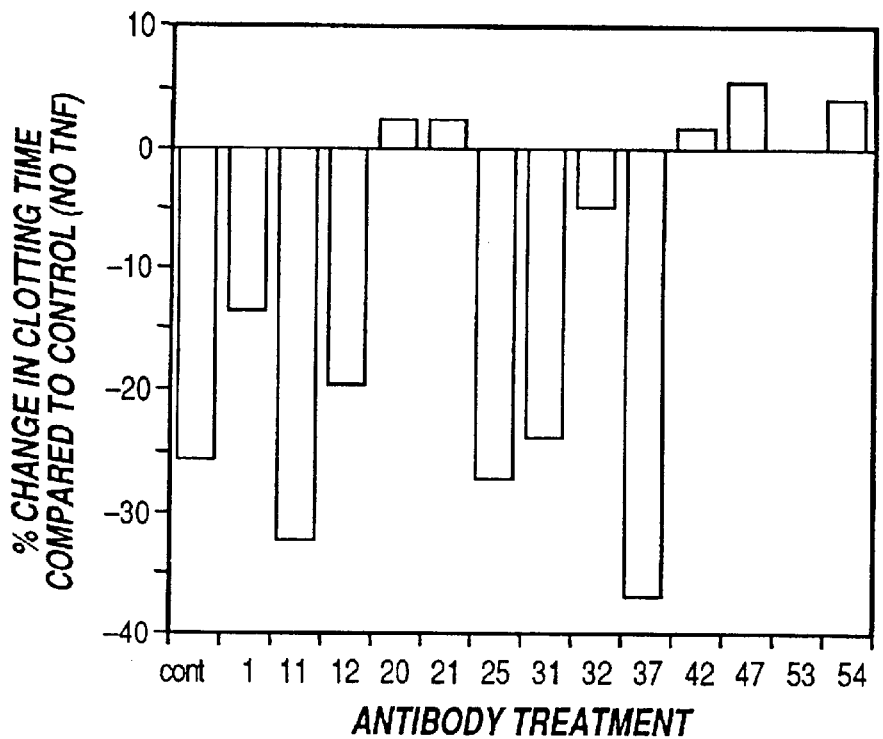
FIG. 6 shows the effect of anti-TNF MAbs on induction of endothelial cell procoagulant activity by TNF.

7. MAb 1 inhibits the induction of procoagulant activity (tissue factor) on cultured bovine aortic endothelial cells (FIG. 6).

Figure 7A:
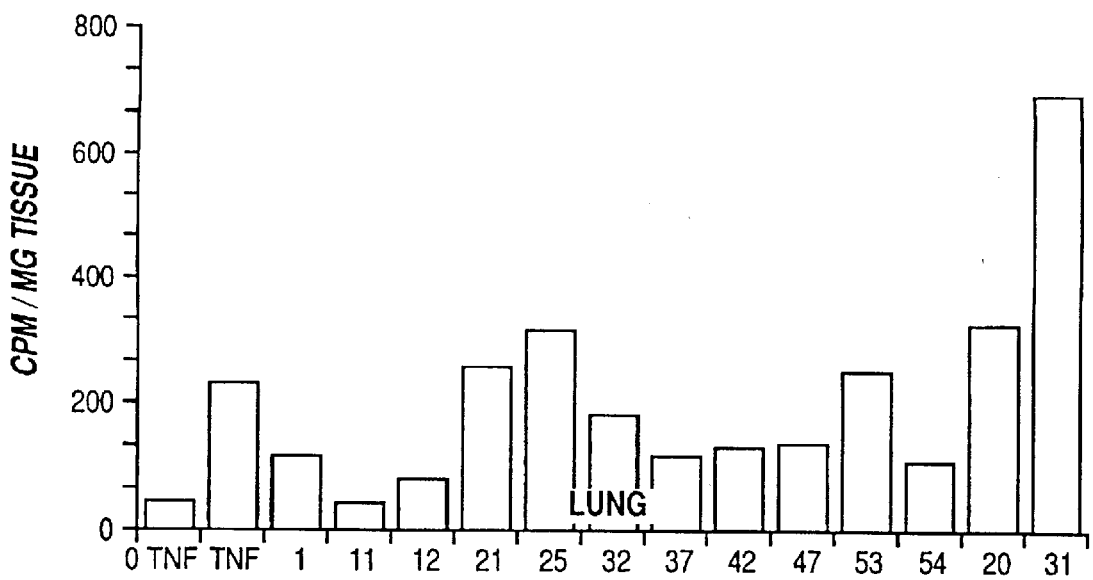
FIGS. 7a, 7b and 7c shows incorporation of labelled fibrinogen into tumours of tumour-bearing mice and the effect of anti-TNF MAbs.
Figure 7B:
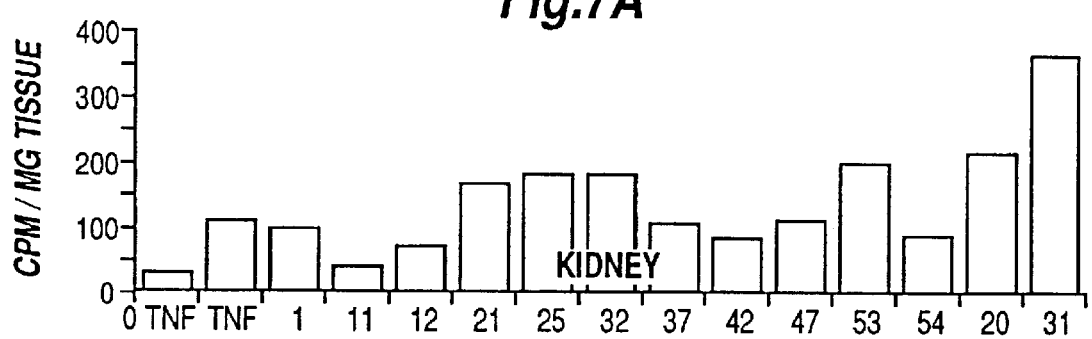
Figure 7C:
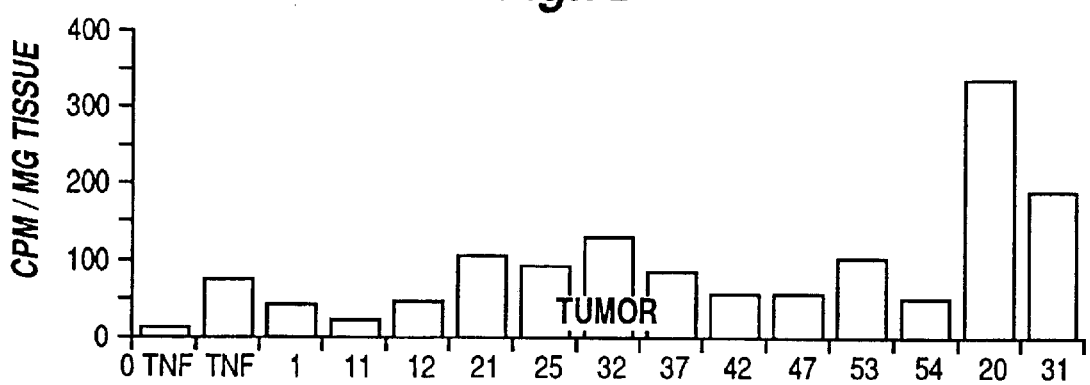

8. MAb 1 reduces the uptake of 125I fibrinogen into tumours of mice treated with TNF (FIGS. 7a–c).

9. MAb 1 competes for binding of 125I TNF and thus shares an overlapping epitope with the following monoclonal antibodies: 21, 25, 32, 47, 54 and 37.

Figure 8:
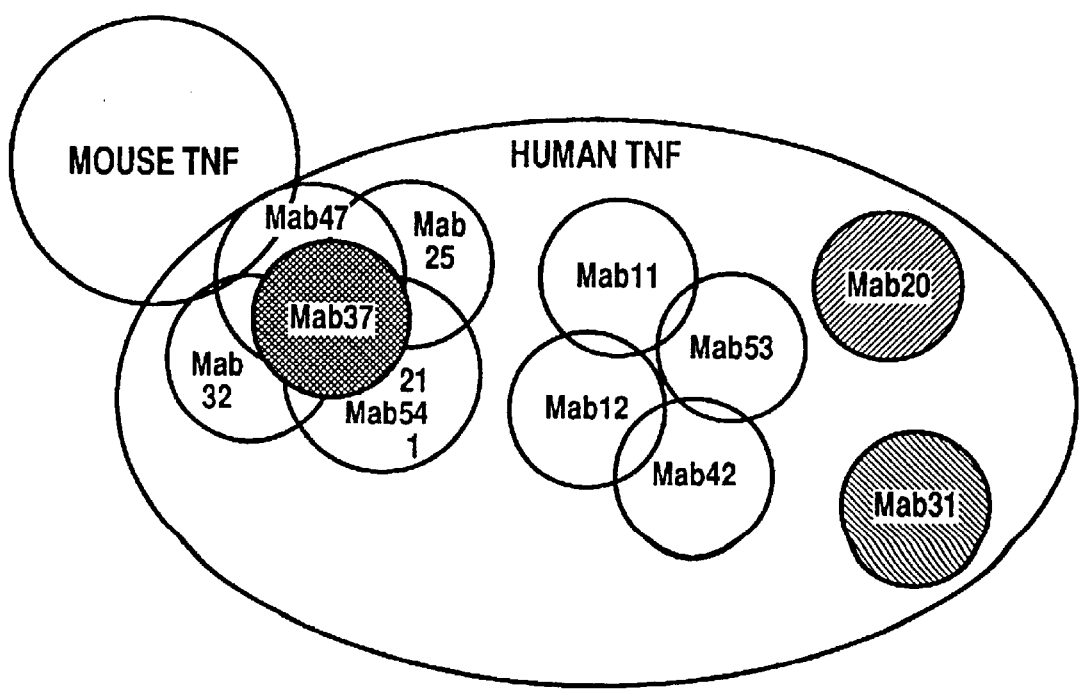
FIG. 8 is a schematic representation of epitopes on TNF.

10. MAb 1 does not compete for binding of 125I TNF with the following monoclonal antibodies: 11, 12, 42, 53, 31 and 20 (FIG. 8).

TABLE 3

RADIORECEPTOR ASSAY:
INHIBITION OF TNF BINDING TO WEHI-164 CELLS BY MAb 1

| TREATMENT | % SPECIFIC BINDING |
|---|---|
| MAb 1 1/10 | 0 |
| 1/100 | 21 |
| 1/1,000 | 49 |
| 1/10,000 | 73 |
| 1/100,000 | 105 |
| cold TNF (ng/tube) | |
| 10,000 | 0 |
| 5,000 | 0 |
| 1,000 | 0 |
| 500 | 10 |
| 100 | 11 |
| 10 | 64 |
| 1 | 108 |
| 0 | 100 |

MAb 32 is an IgG2b, K antibody with an affinity for human TNF alpha of $8.77 \times 10^9$ moles/liter as determined by Scatchard analysis. This monoclonal antibody does not react with either human TNF beta (lymphotoxin) or mouse TNF alpha.

As shown in FIG. 3 MAb 32 does not inhibit TNF cytotoxicity in vitro as determined in the WEHI-164 assay.

Figure 10A:
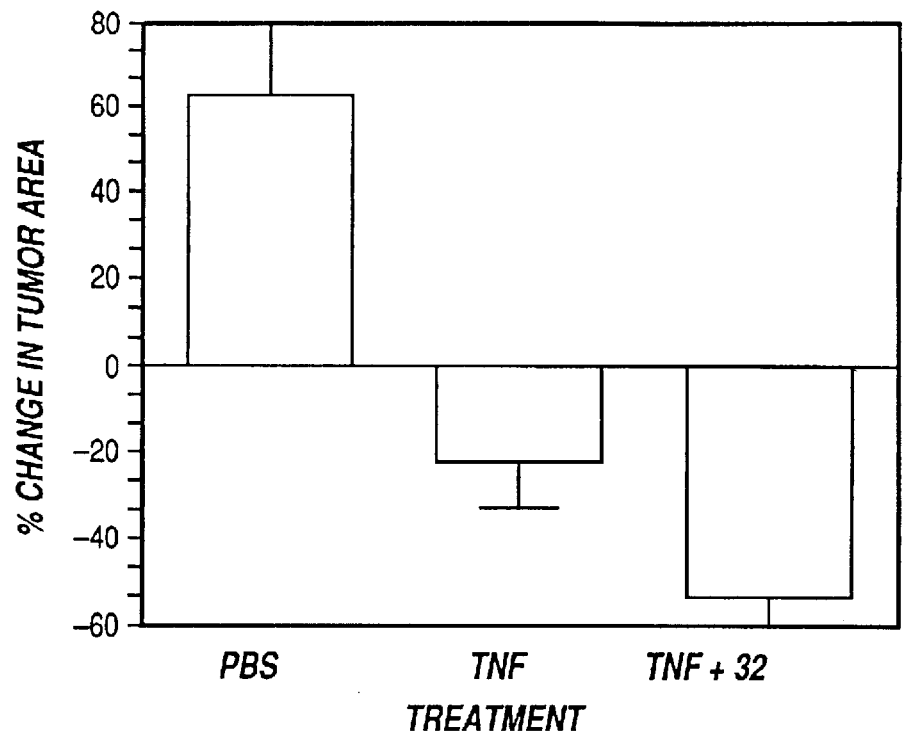
FIGS. 10a and 10b shows the enhancement of TNF regression activity by MAb 32 in two experiments.
Figure 10B:
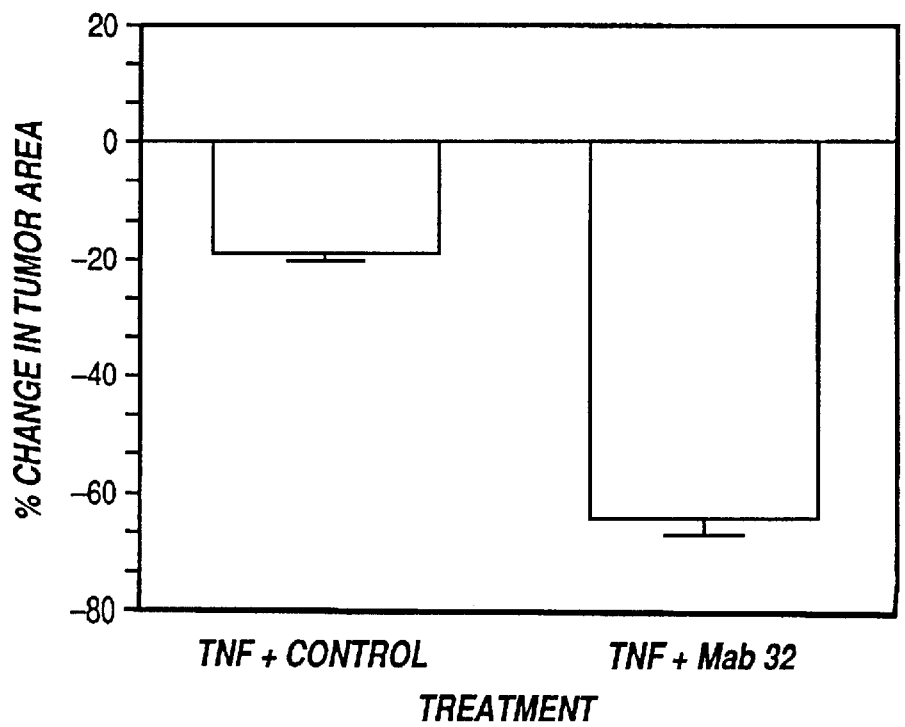

Monoclonal antibody 32 variably enhances TNF-induced tumour regression activity against WEHI-164 fibrosarcoma tumours implanted subcutaneously into BALB/c mice at a TNF dose of 10 ug/day (see FIGS. 10a and 11a–b). This feature is not common to all monoclonal antibodies directed against TNF (FIG. 9) but resides within the binding site specificity of MAb 32 (FIG. 8) which may allow greater receptor mediated uptake of TNF into tumour cells (see Table 4).

TABLE 4

BINDING OF TNF TO RECEPTORS ON WEHI-164 CELLS IN THE PRESENCE OF MAb 32

| | % BINDING$^{125}$ I-TNF | |
|---|---|---|
| MAB DILUTION | CONTROL MAB | MAB 32 |
| 1/10 | 36 | 141 |
| 1/100 | 74 | 88 |
| 1/1000 | 101 | 83 |
| 1/10,000 | 92 | 82 |
| 1/100,000 | 97 | 93 |

Enhancement of TNF activity by MAb 32 at lower doses of TNF is such that at least tenfold less TNF is required to achieve the same degree of tumour regression (see FIGS. 11 and 18). The results for day 1, 2.5 ug and 1 ug TNF and day 2, 5 ug, 2.5 ug and 1ug are statistically significant in a t-test at p<0.01 level. This level of enhancement also increases the survival rate of recipients since the lower dose of TNF used is not toxic. FIG. 19 shows that univalent Fab fragments of MAb 32 also cause enhancement of TNF-induced tumour regression in the same manner as whole MAb 32 (see below).

MAb 32 inhibits the expression of clotting factors on endothelial cells normally induced by incubation of the cultured cells with TNF (see FIG. 6). This response may be mediated by a previously unidentified TNF receptor which is distinct to the receptor found on other cells.

Conversely, MAb 32 enhances the in vivo activation of coagulation within the tumour bed as shown by the incorporation of radiolabelled fibrinogen (FIGS. 7a–c). This may be due to activation of monocytes/macrophage procoagulant and may provide further insight into the mechanism of TNF-induced tumour regression.

The results obtained with MAb 32 are shown in comparison to other anti-TNF MAbs in Table 2.

The ability of MAb 32 and MAb 47 to inhibit the binding of TNF to endothelial cells was also assessed. Bovine aortic endothelial (BAE) cells (passage 11) were plated in 24-well culture dishes (Corning) which had been pre-coated with gelatin (0.2%) and grown to confluence in McCoys 5A (modified) medium supplemented with 20% foetal calf serum. For the radio-receptor assay all dilutions (of cold TNF and MAbs) were made in this medium. The BAE cells were incubated for one hour in the presence of either cold TNF (0 to 100 ng) or MAb (ascites globulins diluted 1/100 to 1/100,000) and iodinated TNF (50,000 cpm). At the end of this time the medium was withdrawn and the cells washed before being lysed with 1M sodium hydroxide. The cell lysate was then counted for bound radioactive TNF. Specific binding of labelled TNF to the cells was then determined.

The results obtained in this assay with MAb 32, MAb 47 and a control MAb are set out in FIG. 12.

The results obtained in the clotting assay using BAE cells cultured in the presence of TNF and anti-TNF MAb correlate with the results obtained in the BAE radioreceptor assay i.e. MAbs which inhibit the induction of clotting factors on the surface of endothelial cells (as shown by the increase in clotting time compared to TNF alone) also inhibit the binding of TNF to its receptor. This is exemplified by MAbs 32 and 47.

MAb 32, which does not inhibit TNF binding to WEHI-164 cells, does inhibit binding of TNF to endothelial cells. This result provides support for the hypothesis that distinct functional sites exist on the TNF molecule and that these sites interact with distinct receptor subpopulations on different cell types. Thus ligands which bind to defined regions of TNF are able to modify the biological effects of TNF by limiting its binding to particular receptor subtypes.

As shown in FIG. 12 MAb 47 is a particularly potent inhibitor of TNF interaction with endothelial cells, the percentage specific binding at a dilution of 1/100 to 1/10,000 being effectively zero.

Receptor Binding Studies of Human TNF Complexed with MAB 32 on Human Carcinoma Cell Lines In Vitro MAb 32 has been shown to enhance the anti-tumour activity of human TNF. The mechanisms behind the enhancement may include restriction of TNF binding to particular (tumour) receptor subtypes but not others (endothelial) with subsequent decrease in TNF toxicity to non-tumour cells. This mechanism does not require enhanced uptake of TNF by tumour cells in in vitro assays. In addition, MAb 32 also potentiates the binding of human TNF directly to TNF receptors on certain human carcinoma cell lines.

Materials and Methods

The following human carcinoma cell lines have been assayed for enhanced receptor-mediated uptake of TNF in the presence of MAb 32: B10, CaCo, HT 29, SKC01 (all colon carcinomas), 5637 (Bladder carcinoma), MM418E (melanoma), IGR3 (melanoma), MCF 7 (breast carcinoma). The cells were propagated in either RPMI-1640 (MM418E) DMEM (CaCo and IGR 3) or Iscoves modified DMEM (B10, HT 29, SK01, S637, MCF 7) supplemented with 10% foetal calf serum, penecillin/streptomycin and L-glutamine. Receptor assays were performed as previously described for endothelial cells except that the incubation time with iodinated TNF was extended to 3 hours for all but the B10 cells for which the radiolabel was incubated for 1 hour.

Results

Enhanced TNF uptake was observed in the presence of MAb32 by the melanoma cell lines tested MM418E and IGR 3 (FIGS. 13 and 14), the bladder carcinoma 5637 (FIG. 15), and the breast carcinoma MCF 7 (FIG. 16). MAb 32 did not affect TNF-receptor interaction in any of the other cell lines as shown by B 10 (FIG. 17) MAb 47, which has been shown to inhibit TNF binding to WEHI-164 cells and endothelial cells, and which also inhibits TNF-mediated tumour regression was found to markedly inhibit TNF binding to all the cell lines tested (FIGS. 13–17).

Conclusions

Receptor binding analyses have indicated a second mechanism whereby MAb 32 may potentiate the anti-tumour activity of TNF. This second pathway for enhancement of TNF results from increased uptake of TNF by tumour all receptors in the presence of MAb 32.

Enhancement of TNF-Mediated Tumour Regression In Vivo by MAB 32 or Univalent FAB' Fragments of MAB 32

Tumour regression studies were carried out as described above in mice carrying WEHI-164 subcutaneous tumours (N=5 animals/group). Tumour size was determined daily during the course of the experiment. The results obtained using MAb 32 are set out in FIG. 22 and show the mean +/−SD % change in tumour area at the completion of treatment (day 2) (■ MAb 32: ▦ control MAb: *MAb 47). Differences observed between control MAb-TNF and MAb 32-TNF treated groups are statistically significant in a T-test at the p-<0.01 level.

The results using the univalent FAb' fragments of MAb 32 are shown in FIG. 19. Tumour size was determined daily during the course of the experiment. The results show the mean SD% change in tumour area at the completion of treatment (day 2). Differences between the control MAb-10F and MAb 32-TNF treated groups are statistically significant in a T-test at the P-<0.01 level.

TNF Induced Tumour Regression: Effect of Anti-Peptide 301 SERA

FIG. 20 shows the percent change in tumour area in tumour-bearing mice treated for three days with TNF plus control MAb (antibody against bovine growth hormone), TNF plus MAb 32 or TNF plus antiserum (globulin fraction) against peptide 301. In an unpaired T-test the control group is significantly different from both of the test groups (MAb 32, antiserum 301) while the MAb 32 and peptide antiserum 301 groups are not significantly different from each other. (control vs MAb 32, p<0.002; control vs antipeptide 301, p<0.025). Thus antisera raised using a peptide which comprises part of the MAb 32 specificity, also causes TNF enhancement of tumour regression.

As shown in FIG. 9 competition binding studies has shown that the thirteen monoclonal antibodies can be subdivided into two main groups, namely MAbs 1, 21, 47, 54, 37, 32 and 25 and MAbs 11, 12, 53 and 42. Experiments were then conducted to identify-the regions on human TNF recognised by these monoclonal antibodies.

Identification of Regions On Human TNF Recognised By Monoclonal Antibodies

Methods

1. Overlapping peptides of 7 and 10 amino acid residues long were synthesized on polypropylene pins according to the method of Geysen et al., 1984, PNAS 81, 3998–4002. The overlap was of 6 and 9 residues respectively and collectively the peptides covered the entire TNF amino acid sequence. The peptides were tested for reactivity with the MAbs by ELISA. MAbs which had TNF reactivity absorbed from them by prior incubation with whole TNF were also tested for reactivity with the peptides and acted as a negative control.

2. Longer peptides of TNF were synthesized as described below. These peptides were used to raise antisera in sheep using the following protocol. Merino sheep were primed with TNF peptide conjugated to ovalbumin and emulsified in Freunds Complete adjuvant and boosted at 4 weekly intervals with peptide-ovalbumin and sera assayed for the presence of anti-TNF antibody by radioimmunoassay. Of the peptides shown only peptides 275, 301, 305, 306 and 307 elicited sera reacting with whole TNF. The positive sera were then used in competitive binding assays (PACT assays) with the MAbs.

The following peptides were synthesised and are described using the conventional three letter code for each amino acid with the TNF sequence region indicated in brackets.

Peptide 275
  H-Ala-Lys-Pro-Trp-Tyr-Glu-Pro-Ile-Tyr-Leu-OH (111–120)

Peptide 301
  H-Val-Arg-Ser-Ser-Ser-Arg-Thr-Pro-Ser-Asp-Lys-Pro-Val-Ala-His-Val-Val-Ala-OH (1–18)

Peptide 302
  H-Leu-Arg-Asp-Asn-Gln-Leu-Val-Val-Pro-Ser-Glu-Gly-Leu-Tyr-Leu-Ile-OH (43–58)

Peptide 304
  H-Leu-Phe-Lys-Gly-Gln-Gly-Cys-Pro-Ser-Thr-His-Val-Leu-Leu-Thr-His-Thr-Ile-Ser-Arg-Ile-OH (63–83)

Peptide 305
  H-Leu-Ser-Ala-Glu-Ile-Asn-Arg-Pro-Asp-Tyr-Leu-Asp-Phe-Ala-Glu-Ser-Gly-Gln-Val-OH (132–150)

Peptide 306
  H-Val-Ala-His-Val-Val-Ala-Asn-Pro-Gln-Ala-Glu-Gly-Gln-Leu-OH (13–26)

Peptide 307
  H-Ala-Glu-Gly-Gln-Leu-Gln-Trp-Leu-Asn-Arg-Arg-Ala-Asn-Ala-Leu-Leu-Ala-Asn-Gly-OH (22–40)

Peptide 308
  H-Gly-Leu-Tyr-Leu-Ile-Tyr-Ser-Gln-Val-Leu-Phe-Lys-Gly-Gln-Gly-OH (54–68)

Peptide 309
  H-His-Val-Leu-Leu-Thr-His-Ile-Ser-Arg-Ile-Ala-Val-Ser-Tyr-Gln-Thr-Lys-Val-Asn-Leu-Leu-COOH (73–94)

Peptide 323
  H-Thr-Ile-Ser-Arg-Ile-Ala-Val-Ser-Tyr-Gln-Thr-COOH (79–89)

These peptides were synthesised using the following general protocol.

All peptide were synthesised using the Fmoc-polyamide method of solid phase peptide synthesis (Atherton et al, 1978, J.Chem.Soc.Chem.Commun., 13, 537–539). The solid resin used was PepSyn KA which is a polydimethylacrylamide gel on Kieselguhr support with 4-hydroxymethylphenoxy-acetic acid as the functionalised linker (Atherton et al., 1975, J.Am.Chem. Soc. 97, 6584–6585).

The carboxy terminal amino acid was attached to the solid support by a DCC/DMAP-mediated symmetrical-anhydride esterificatidn.

All Fmoc-groups were removed by piperidine/DMF wash and peptide bonds wereformed either via pentafluorophenyl active esters or directly by BOP/NMM/HOBt (Castro's reagent) (Fournier et al, 1989, Int.J.Peptide Protein Res., 33, 133–139) except for certain amino acids as specified in Table 5.

Side chain protection chosen for the amino acids was removed concomittantly during cleavage with the exception of Acm on cysteine which was left on after synthesis.

TABLE 5

| Amino Acid | Protecting Group | Coupling Method |
| --- | --- | --- |
| Arg | Mtr or Pmc | Either |
| Asp | OBut | Either |
| Cys | Acm (permanent) | Either |
| Glu | OBut | Either |
| His | Boc | OPfp only |
| Lys | Boc | Either |
| Ser | But | BOP only |
| Thr | But | BOP only |
| Tyr | But | Either |
| Trp | none | Either |

TABLE 5-continued

| Amino Acid | Protecting Group | Coupling Method |
|---|---|---|
| Asn | none | OPfp only |
| Gln | none | OPfp only |

Cleavage and Purification

Peptide 301, 302, 305 are cleaved from the resin with 95% TFA and 5% thioanisole (1.5 h) and purified on reverse phase C4 column, (Buffer A—0.1% aqueous TFA, Buffer B—80% ACN 20% A).

Peptide 303, 304 are cleaved from the resin with 95% TFA and 5% phenol (5–6 h) and purified on reverse phase C4 column. (Buffers as above).

Peptide 306, 308 are cleaved from the resin with 95% TFA and 5% water (1.5 h) and purified on reverse phase C4 column. (Buffers as above).

Peptide 309 Peptide was cleaved from the resin with 95% TFA and 5% thioanisole and purified on reverse phase C4 column. (Buffers as above).

Peptide 307 Peptide was cleaved from the resin with a mixture of 93% TFA, 3.1% Anisole, 2.97% Ethylmethylsulfide and 0.95% Ethanedithiol (3 h) and purified on reverse phase C4 column. (Buffers as above).

Results

Typical results of MAb ELISA using the 7 and 10 mers are shown in FIGS. 21a–c. Together with the results of PACT assats using the sheep anti-peptide sera (shown in Table 6) the following regions of TNF contain the binding sites of the anti-TNF MAbs.

Mab 1: residues 1–18, 58–65, 115–125, 138–149
Mab 11: residues 49–98
Mab 12: residues 22–40, 70–87
Mab 21: residues 1–18, 76–90
Mab 25: residues 12–22, 36–45, 96–105, 132–157
Mab 32: residues 1–26, 117–128, 141–153
Mab 37; residues 22–31, 146–157
Mab 42: residues 22–40, 49–96, 110–127, 136–153
Mab 47: residues 1–18, 108–128
Mab 53: residues 22–40, 69–97, 105–128, 135–155
Mab 54: residues 56–79, 110–127, 136–155

TABLE 6

COMPETITIVE BINDING OF TNF BY ANTI-TNF MONO-
CLONES IN THE PRESENCE OF ANTI PEPTIDE SERA

| MAB/PEPTIDE SERA | 275 | 301 | 305 | 306 | 307 |
|---|---|---|---|---|---|
| 1 | − | + | − | − | − |
| 11 | − | +/− | − | − | − |
| 12 | − | + | − | − | ++ |
| 21 | − | ++ | − | − | − |
| 25 | − | + | − | − | − |
| 32 | − | ++++ | + | + | − |
| 37 | − | + | +/− | − | + |
| 47 | − | + | − | − | − |
| 53 | − | + | − | − | + |
| 54 | − | + | − | − | − |
| 42 | − | + | + | − | + |

Note 1:
− indicates no competition,
+ indicates slight competition at high concentration of anti-peptide antisera (1/50),
++++ indicates strong competition by anti-peptide sera equal to that of the homologous MAb.
Note 2:
Only peptide which elicited sera recognising whole TNF were used in this assay.

As will be understood by persons skilled in this field the ligands of the present invention can be used in assays of biological fluids for detecting the presence of and quantifying the concentration of TNF in a sample. One means by which this may be achieved is by using the ligands of the present invention in conventional ELISAs. Set out below is an example of such an assay.

| TNF ELISA REAGENTS | | |
|---|---|---|
| CARBONATE COATING BUFFER, pH 9.6 | | |
| $Na_2CO_3$ | 1.6 g | Add 800 mL $dH_2O$, pH to 9.6 |
| $NaHCO_3$ | 2.9 g | then make to 1 L with $dH_2O$ |
| BLOCKING BUFFER | | |
| BSA | 1 g | Add BSA to PBS and allow |
| PBS | 100 mL | to dissolve fully before using. Store at 4° C. |
| WASH BUFFER (0.05% Tween/PBS) | | |
| Tween 20 | 0.5 g | Add Tween to PBS and mix |
| PBS | 1 L | thoroughly before use |
| CITRATE BUFFER | | |
| Citric Acid. $1H_2O$ | 2.1 g in 50 mL $dH_2O$ | Add solutions together and adjust |
| TriSodium Citrate $2H_2O$ | 1.47 g in 50 mL $dH_2O$ | pH to 4.0–4.2 |

NB: All incubations can be carried out at 4° C. overnight OR at room temperature for 2 hrs OR at 37° C. for 1 hr.

Method

Coat ELISA plates with equal proportions of MAb1, MAb32 and MAb54 to human TNF in carbonate coating buffer. The total immunoglobulin concentration should be 20 μg/mL and 100 μL is added to each well. Cover plates and incubate.

Wash plates 3× with PBS/Tween.

Incubate plates with 250 μL/well blocking buffer

Wash plates 3× with PBS/Tween.

Add 100 μL sample or TNF standards, diluted in blocking buffer where required, to plates, then cover and incubate.

Wash plates 3 × with PBS/Tween.

Add 100 μL biotinylated antibody mix (equal proportions of biotinylated monoclonal antibodies 11 & 42 to human TNF) at a final concentration of 10 μg/mL in blocking buffer to each well, cover and incubate.

Wash plates 3× with PBS/Tween.

Add 100 μL/well streptavidin-peroxidase (Amersham product no. RPN 1231) at 1/2,000 in blocking buffer, then cover and incubate.

Wash plates 3 × with PBS/Tween.

Add 100 μL/well biotinylated anti-stretpavidin monoclonal antibody (Jackson Immunoresearch) at 1/40,000 in blocking buffer, cover and incubate.

Wash plates 3 × with PBS/Tween.

Add 100 μL/well streptavidin-peroxidase at 1/2,000 in blocking buffer, cover and incubate.

Wash plates 3 × with PBS/Tween.

Add 100 μL/well peroxidase substrate (ABTS) at 1 mg/mL in citrate buffer containing 0.3 μL/ml $H_2O_2$ and leave to incubate at room temperature for up to 1 hour.

NB: Substrate solution should be prepared immediately prior to use.

Read absorbance at 405 nm, and compare sample readings with TNF standard curve to determine TNF levels.

| BIOTINYLATION OF IgG | | |
|---|---|---|
| 50 mM BICARBONATE BUFFER, pH 8.5 | | |
| $Na_2CO_3$ | 1.6 g | |
| $NaHCO_3$ | 2.9 g | In 1 L $dH_2O$, adjust pH with HCl |
| 0.1 PHOSPHATE BUFFER, pH 7.0 | | |

Method

Prepare immunoglobulins by purifying on a protein A column, then freeze-drying.

Reconstitute the immunoglobulins with 50 mM bicarbonate buffer to a concentration of 20 mg/mL in a clean glass test tube.

Add 0.4 mg biotin per 20 mg Ig directly to the tube.

Place the test tube on ice and incubate for 2 hours.

Remove the unreacted biotin by centrifuging at 1000 g for 15–30 minutes in a Centricon-30 microconcentrator. Dilute the sample in 0.1 M phosphate buffer and repeat the centrifugration twice.

Make the sample up to the original volume with phosphate buffer, add 0.1% $NaN_3$ and store at 4° C. until used.

The results obtained in such an assay using samples containing known amounts of TNF is shown in FIG. 34.

As mentioned above the specific mouse monoclonal antibodies disclosed in this application can be humanised if required. A number of methods of obtaining humanised antibodies are set out in PCT/GB92/01755 (WO93/06213). A humanised version of MAb32 designated VHP3-VλA2 was produced by the method disclosed in PCT/GB92/01755. Briefly, this antibody was produced as follows:

1 Cloning and Display of the V Genes of MAb 32 on Phage

The genes of the mouse MAb32 antibody (IgG2b, Kappa) were rescued by PCR essentially as described (Clackson et al., 1991, in "PCR: A Practical Approach" eds. M. J. McPherson et al., IRL Press, Oxford, pp 187–214) using the primers VH1BACk and VH1FOR2 for the VH gene and Vk2BACK and VK4FOR for the VL gene and the polymerase chain reaction (PCR, R. K. Saiki et al., 1985, Science 230, p1350). The mouse VH and Vk genes were assembled for expression as scFv fragments by PCR assembly (Clackson et al., supra) amplified with VH1BACKSfi and VFFOR4NOT and ligated into phagemid pHEN1 (H. R. Hoogenboom et al., 1991 Nucl. Acids. Res. 19 pp4133–4137) as a SfiI-NotI cut restriction fragment, and electroporated into E.coli HB2151 cells. Of 96 clones analysed by ELISA (see below), 9 secreted TNF-binding soluble scFv fragments. Sequencing revealed in all clones a mouse VH of family IIB and a mouse Vk of family VI (E. A. Kabat et al., 1991 Sequences of Proteins of Immunological Interest, US Public Health Services). Nucleotide mutations which were probably introduced by the PCR were detected by comparing the 9 sequences, and a clone with consensus sequence and binding activity (scFv-MAb32) chosen for further cloning experiments.

Recloning of the MAb32 V-genes for soluble expression:

The murine V-genes were recloned for soluble expression of heavy (Fd, VHCH1) or light chain, by linking the mouse V-genes to the human CH1 (of the mu-isotype) or human Ck gene respectively by splice overlap extension. The mouse Vk gene was amplified from scFv-MAb32 DNA with oligonucleotides MOJK1FORNX (binds in joining region of V-gene and MVKBASFI (binds in 5' region and adds SfiI restriction site); the human Ck was obtained by PCR from a mouse-human chimaeric light chain gene (of NQ10.12.5, described in Hoogenboom et al., 1991 supra), with oligonucleotides MOVK-HUCK-BACK (binds in 5' of human Ck and is partially complementary with mouse Jk 1 region) and HUCKNOT16NOMYC (sits in 3' end of human Ck, retains the terminal cysteine, and tags on a NotI restriction site) as in Clackson et al., 1991 using a two fragment assembly. For linkage of the DNA fragments, the two PCR fragments were mixed and amplified with MVKBASFI and HUCKNOT16NOMYC. The chimaeric VkCk gene was subsequently cloned asa SfiI-NotI fragment in pUC19 derivative containing the pe1B signal peptide sequence and appropriate cloning sites for soluble expression of the light chain (pUC19-pe1B-myc). Similarly, the mouse VH gene (amplified from scFv-MAb32 with LMB3 and VH1FOR-2) was combined by splicing by overlap extension PCR with the human u-CH1 domain (amplified from human IgM-derived cDNA (Marks et al., 1991, supra; WO 92/01047) with Mo-VH-Ku-CH1 and HCM1FONO, and cloned as SfiI-NotI fragment into a pUC19-pe1B-myc for soluble expression of a tagged chain.

Display of the MAb32 Antibody on Phage

The chimaeric light chain was displayed on phage fd by reamplification of the mouse/human chimaeric chain with HUCKCYSNOT and MVKBAAPA and cloning into fd-tet-DOG1 as an ApaLI-NotI fragment. Cells harbouring a plasmid with the heavy Fd chain gene were grown in 2×TY containing AMP-GLU (1%) to logarithmic phase (OD600 of 0.5) and infected with a 20-fold excess of light-chain displaying phage. After 45 min at 37° C. without shaking and 45 min at 37° C. with shaking in the 2×TY, ampicillin (100 μg/ml). Glucose 1% medium, a sample was diluted into 50-fold volume of prewarmed (37° C.) 2×TY, ampicillin (100 μg/ml) and tetracyclin (15 μg/ml), grown for 1 hr at 37° C. and then overnight at 30° C. (shaking). Phage particles collected from the supernatant of such culture displayed TNF-binding Fab fragments anchored through the light chain on their surface.

Similarly, the reversed configuration was made. The heavy chain VHCH1 fragment was cloned into fd-tet-DOG1

(after amplification of the Fd chain gene from the mouse/human chimeric construct with VH1BACKAPA and HCM1FONO), and phage used to infect cells capable of producing soluble light chain. Phage particles collected from the supernatant of such culture displayed TNF-binding Fab fragments anchored through the heavy chain VHCH1 fragment on their surface.

Properties of MAb 32 fragments displayed on phage:

The V-genes of the murine antibody MAb32 were cloned by amplifying the hybridoma V-genes, cloning the VH and Vk genes as scFv fragments in phagemid pHEN1 as above. Antibody scFv fragments which bind to TNF were identified by ELISA. The mouse VH gene was recloned in pUC19-pe1B-myc for soluble expression as a mouse VH linked to human mu-CH1, while the light chain was recloned with the human Ck domain in vector fd-tet-DOG1 as a fusion with g3p. When cells harbouring the heavy chain construct were infected with the fd-phage carrying the light chain, phage particles emerged which carried light chain-g3p associated with the fd heavy chain. Indeed, binding to TNF and the 301 peptide was retained, as judged by ELISA with phage displaying the mouse-human chimaeric Fab fragment. In the phage ELISA, the background signal of phage carrying the light chain only was a lightly higher than wild-type fd-tet-DOG1 phage, but always lower than the signal obtained with Fab-displaying phage. Similarly, TNF binding phage was made with the heavy chain VHCH1 fragment anchored on phage, and the light chain provided as a soluble fragment. Hence, MAb32 is functional in the dual combihatorial format in both display orientations.

2 Chain Shuffling by Epitope Imprinted Selection (EIS) Construction of One Chain-Libraries Kappa, lambda light chain and Mu-specific CDNA was made from the mRNA prepared from the peripheral blood lymphocytes from two healthy donors essentially as in Marks et al., 1991, supra. The first-strand CDNA synthesis was performed with oligonucleotides HCM1F0, HUCLCYS and HUCKCYS for Mu-specific, lambda and kappa libraries respectively. The VH-CH 1 repertoire was amplified from this cDNA with oligonucleotides HCM1OF and six family specific VHBACK primers (as in Marks et al., 1991, supra), reamplified with a NotI-tagged forward primer (HCM1FONO) and ApaLI tagged VHBACK primers (6 primers HuVH1BAAPA to HuVH6BAAPA). Similarly, the light chain repertoires were amplified with HUCLCYS or HUCKCYS forward primers and HUVλ1BACK to HuVλ6BACK or HuVk1BACK to HuVk6BACK back primers described in Marks et al., 1991, supra and PCT/GB91/01134 (WO 92/01047). In each case described in this section the lambda and kappa chain variable repertoires were amplified separately. The amplified repertoires were reamplified with ApaLI and NotI tagged versions of these oligonucleotides (13 back primers HuVλ1BAAPA to Huλ6BAAPA or HuVk1BAAPA to HuVkBAAPA and two forward primers HUCLCYSNOT and HuCKCYSNOT, respectively). All three repertoires were cloned into vector fd-tet-DOG1 as ApaLI-NotI fragments, and electroporated into $E.coli$ MC1061 cells, to obtain libraries of $1.0 \times 10^7$ clones for VλCA, $1.4 \times 10^6$ clones for VkCk, and $5 \times 10^6$ clones for IgM-derived VHCH1. The presence of insert was checked and the frequency of inserts in the library found to be higher than 95% inall three cases.

Selecting a Human VL using the Mouse VH Domain as Docking Chain

In a first chain shuffling experiment, the mouse VH (linked to the human CH1 domain), expressed from pUC19-pe1B-myc, was paired as Fab fragment with a library of $10^7$ different human VλCλ domains. Phage displaying the antibody fragments were subjected to rounds of panning on TNF-coated tubes. By following the titre of the eluted phage, the extent of selection was monitored. After 4 rounds (with a 100-fold increase in the titre of eluted phage), 24 out of 28 individual clones were found to be binding to TNF in an ELISA with phage expressing Fab fragments (all with the mouse VH-human CH1). Phage only displaying the selected human VλCλ domains gave a background similar to phage displaying only the chimaeric mouse Vk-human Ck. Sixteen clones taken after the first round of selection were found to be negative.

Only three different BstN1 fingerprints were found amongst the 24 binders, with one pattern-dominating (21/24). Light chains VλA2, VλC4 and VλD1 were found with frequencies of 21/24, 2/24 and 1/24 respectively. Sequencing revealed that all three light chains are derived from the same germline gene, a human Vλ1-1-1. Clone VλC4 has 1, clone VλD1 has 2 and clone VλA2 7 amino-acid residue differences from the germline. However, clone VλA2 uses a framework-1 region which more closely resembled the germline sequence of a related Vλ1, humv1117, and therefore may be the result of a cross-over. The germline character of the clones was also noted in the CDR3 sequence, with minimal variation in sequence and no length variation between the three clones. Apparently, only a very limited number of genes with very similar sequences fix the stringent requirements (being compatible with the mouse VH and forming an antigen-binding pair).

Selecting a Human VH Using the Selected Human VL Domains as Docking Chains

Three selected Vλ genes were recloned in pUC19-pe1B-myc for soluble expression VλCλ chains. $E.coli$ cells harbouring the three light chain plasmids were mixed, infected with a phage library of human VHCH1 genes, expressed from the fd-tet-DOC1 library described earlier and the library subjected to rounds of panning on TNF-coated Immuno tubes. Clones were picked after 5 rounds, when the titre of eluted phage increased 100-fold. Fifteen out of 20 clones analysed by BstNI fingerprint of the DNA insert used one of two patterns (with approximately the same frequency). The 15 clones when combining their heavy chain VHCH1 fragments with the VλA2 light chain gave stronger phase ELISA signals than when combined with the VλC4 or VλD1 light chain. Background signals obtained with phage displaying the heavy chain VHCH1 fragment only were similar to the signal of the murine VH-human CH1.

Sequencing revealed that the two patterns could be assigned to three unique human VH sequences (clones VHP1/2/3, with clone VHP1 having a BstNI fingerprint which is nearly identical to that of clone VHP2). Like the selected light chain genes, the selected heavy chain genes are derived from the same germline VH gene (germline DP-51 from the VH3 family, Tomlinson et al., J. Mol. Biol. 227, pp776–798 1992), with minimal residue differences. The selected human V-genes were aligned to their closest germline homologue; identical residues in the selected genes are represented by hyphens. Framework 4 of the $V_H$ genes was truncated at 4th residue. Clone VHP1 was most likely a cross-over between DP-51 and a related germline, DP-47. All three selected VH-genes had relatively short CDR3 loops (8, 9 and 10 residues), but shared little homology in this sequence.

Specificity of Binding of the Selected V-gene Pairs

A specificity ELISA with MAb32 and soluble ScFv fragments on a number of antigens showed that MAb32, its ScFv-derivative and three of the humanised TNF-binders (as ScFv-fragments) bind specifically to TNF. No significant binding was obtained to ELISA plates coated with keyhole limpet haemocyanin, ovalbumin, cytochrome c. bovine serum albumin, human thyroglobulin, or 2-phenyloxazol-5-one-BSA or to plastic only. Fully humanized clones were obtained which bound to both peptide 301 and TNF.

In addition, to show that the human scFv fragments compete with the original antibody for binding to TNF, the binding of the scFv constructs in a competition ELISA with the Fab fragment derived by proteolytic cleavage of MAb32 was analysed. Single chain Fv fragments were incubated on a TNF-coated surface with increasing amounts of the Fab fragment and the amount of bound scFv detected in ELISA. Each of the scFv fragments competed with the FabMAb32 for binding to TNF, including both the original scFv-MAb32 and the humanised scFv fragments.

Thus the fine specificity of MAb32 for peptide 301 of TNF was retained through the humanisation process.

Affinity of Binding of the Selected V Gene Pairs

MAb32 and purified, monomeric forms of the recombinant mouse scFv-MAb32 and the human scFv antibodies VHP1-V$\lambda$A2. VHP2-V$\lambda$A2 and VHP3-V$\lambda$A2, were subjected to competition ELISA for the determination of the relative affinity for TNF. Antibodies were incubated on a TNF-coated surface in the presence of increasing amounts of soluble TNF. All the clones showed a roughly similar decrease in the ELISA signal over the same range of increasing TNF concentrations (with an IC50 in the 10 nM to 100 nM range).

MAb32 and VHP3V$\lambda$A2 fragments were also analysed for binding properties using the Pharmacia BIAcore. TNF was indirectly immobilised on the surface, and the binding of antibody monitored. On the TNF surface, the Fab fragment from MAb32 by proteolytic cleavage and the scFv MAb32 showed very similar fast off rates (approximately $10^{-2}s^{-1}$). The human VHP3-V$\lambda$A2 antibody has an off rate in the same range as the original scFv-MAb32. On rates for antibody protein interactions were in the range seen for the interaction between other proteins and their receptors, and cover a 100 fold range between $10^4$ and $10^6$ $M^{-1}S^{-1}$ (Mason D. W. and Williams, A. F., 1986, Kinetics of Antibody Reactions and the Analysis of Cell Surface Antigens, Blackwell, Oxford; Pecht, I., 1992 in Sela, M. (ed), Dynamic Aspects of Antibody Function, Academic Press Inc., New York, Vol. 6 pp 1–68). Assuming the on rates of the antibody TNF interactions are typical of antibody protein interactions, the off rate derived by the BIACore analysis is consistent with the affinity indicated by the competition ELISA ($Kd \cong 10^{-7}$ to $10^{-8}M$).

Thus, these determinations are consistent with scFvMAb32 and the humanised scFv clone VHP3-V$\lambda$A2 having a similar affinity and thus with the retention of affinity, as well as specificity, through epitope imprinted selection.

Conclusion

We have shown that a mouse antibody can be rebuilt into a human antibody with the same specificity by the process of epitope imprinted selection (EIS).

A library of human light chains were shuffled with a mouse VH domain, binding combinations selected and then used in a second shuffle as "docking domains" for a library of human VH genes. Completely human antibodies were isolated from such "genuine" human library. The antibodies were shown to bind retain binding specificity. Alternatively, the mouse VL was used as docking chain for selecting human VH partners. Such VH domains can be used to find human VL genes, or alternatively, can be combined with human VL domains selected with the mouse VH domain. Indeed, binding activity was obtained by combining two independently selected V-genes, pointing towards potential additivity of the EIS procedure.

The EIS approach may serve to humanise antibodies more rapidly than by CDR-grafting (Riechmann et al., 1988, supra), as this method requires very often a detailed knowledge of the 3-D structure of the antibody. However, the EIS method can be extended to for example antibody repertoires obtained by phage selection from immunised rodents. Following immunisation with antigen, a repertoire of V-genes with high affinity and specificity may be selected and then used in an epitope imprinted selection (see example 4) to generate a range of human antibodies of high affinity and enriched for the desired specificity.

Enhancement of TNF-Induced Tumour Regression by Antibody VHP3-V$\lambda$A2, the Human Equivalent of MAB 32

BALB/c mice wer e inoculated with WEHI-164 tumour cells as described above. After development of subcutaneous tumours the micewere treated daily with TNF (1 or 10 $\mu$g) alone or in combination with purified P3A2 (50$\mu$) by intraperitoneal injection. Tumour size was measured throughout the course of the treatment period.

Results are shown in FIG. 35.

VHP3-V$\lambda$A2 enhanced the anti-tumour activity of TNF at both the 1 and 10 $\mu$g levels.

Conclusions

Mapping of the regions recognised by each of the MAbs has indicated that tAbs in group I (MAbs 1, 21, 47, 54, 37, 32 and 25 as show n on the schematic diagram bind TNF in theuregion of residues 1–18 with the exception of MAbs 37 and 54, while MAbs in group II of the schematic diagram (MAbs 11, 12, 53 and 42) bind TNF in the region of residues 70–96 which encompasses a so-called pallendromic loop on the TNF 3-D structure. MAbs which inhibit the induction of endothelial cell procoagulant activity (MAbs 1, 32, 42, 47, 54 and 53) all bind in the region of residues 108–128 which again contains a loop structure in the 3-D model and may indicate that this region interacts with TNF receptors which are found on endothelial cells but not tumour cells. MAb 32 which potentiates the in viva tumour regression andanti-viral activity of TNF is the only antibody which binds all the loop regions associated with residues 1–26, 117–128, and 141–153 and hence binding of these regions is crucial for enhanced TNF bioactivity with concommittant reduction of toxicity for normal cells.

As is apparent from Table 2 MAb 1, 47 and 54 have the same effect on the bioactivity of TNF. From the results presented above it is noted that these three monoclonals bind to similar regions of the TNF molecule. Accordingly, it is believed that a ligand which binds to TNF in at least two regions selected from the group consisting predominately of the region of residues 1–20, the region of residues 56–77, the region of residues 108–128 and the region of residues 138–149 will effect the bioactivity of TNF in a manner similar to that of MAbs 1, 47 and 54. Similarly, it is believed that a ligand which binds to TNF predominately in the regions of residues 1–20 and 76–90 will have the same effect on the bioactivity of TNF as MAb 21. A ligand which binds to TNF predominately in the regions of residues 22–40 and 69–97 will have the same effect on bioactivity of TNF as MAb 12. A ligand which binds to TNF predominately in the regions of residues 1–30, 117–128, and 141–153 would be expected to have the same effect on the bioactivity of TNF as MAb 32 and a ligand which binds to TNF predominately in the regions of residues 22–40, 49–97, 110–127 and 136–153 would be expected to have the same effect on the bioactivity of TNF as MAb 42. A ligand which binds to TNF predominately in the regions of residues 22–31 and 146–157 would be expected to have the same effect on the bioactivity of TNF as MAb 37 and a ligand which binds to TNF predominately in the regions of residues 22–40, 69–97, 105–128 and 135–155 would be expected to have the same effect on the bioactivity of TNF as MAb 53.

The present inventors have quite clearly shown that the bioactivity of TNF can be altered by the binding of a ligand to the TNF, and that the effect on the bioactivity is a function of the specificity of the ligand. For example, the binding of MAb 32 to TNF in the regions of residues 1–26, 117–128 and 141–153 results in the induction of endothelial procoagulant activity of the TNF and binding of TNF to receptors on endothelial cells being inhibited; the induction of tumour fibrin deposition and tumour regression activities of the TNF being enhanced; the cytotoxicity being unaffected and the tumour receptor binding activities of the TNF being unaffected or enhanced. It is believed that this effect on the bioactivity of the TNF may be due to the prevention of the binding of the epitope of the TNF recognised by MAb 32 to naturally occurring biologically active ligands. Accordingly, it is believed that a similar effect to that produced by MAb 32 could also be produced by a ligand which binds to a region of TNF in a manner such that the epitope recognised by MAb 32 is prevented from binding to naturally occurring biologically active ligands. This prevention of binding may be due to steric hindrance or other mechanisms.

Accordingly, it is intended that the prevention of the binding of epitopes recognised by the various monoclonal antibodies described herein to naturally occurring biologically active ligands is within the scope of the present invention.

We claim:

1. An isolated antibody or fragment thereof which binds a peptide consisting of residues $Leu_{63}$-$Phe_{64}$-$Lys_{65}$-$Gly_{66}$-$Gln_{67}$-$Gly_{68}$-$Cys_{69}$-$Pro_{70}$-$Ser_{71}$-$Thr_{72}$-$His_{73}$-$Val_{74}$-$Leu_{75}$-$Leu_{76}$-$Thr_{77}$-$His_{78}$-$Thr_{79}$-$Ile_{80}$-$Ser_{81}$-$Arg_{82}$-$Ile_{83}$ (peptide 304) of matture human TNF-α.

* * * * *

UNITED STATES PATENT AND TRADEMARK OFFICE
CERTIFICATE OF CORRECTION

PATENT NO. : 6,593,458 B1
DATED : July 15, 2003
INVENTOR(S) : Deborah A. Rathjen et al.

It is certified that error appears in the above-identified patent and that said Letters Patent is hereby corrected as shown below:

Column 2,
Line 43, please replace "6829" with -- 8829 --.

Column 5,
Line 36, please replace "topagraphic" with -- topographic --.

Column 9,
Line 39, please replace "MAb47" with -- MAb 47 --.

Column 11,
Line 52, please replace "wasadded" with -- was added --.

Column 12,
Line 2, please replace "was discarded s" with -- was discarded --.
Line 20, please replace "37° C.," with -- 37° C, --.

Column 13,
Line 47, please replace "butnohua" with -- but not human --.

Column 14,
Line 53, please replace "8.77 x $10^9$" with -- 8.77 x $10^{-9}$ --.

Column 16,
Line 46, please replace "ofthe" with -- of the --.

Column 17,
Line 1, please replace "FIG. 22" with -- FIG. 18 --.
Line 34, please replace "identify–the" with -- identify the --.

Column 18,
Line 45, please replace "esterificatidn" with -- esterification --.
Line 47, please replace "wereformed" with -- were formed --.

Column 19,
Line 34, please replace "Typical,results" with -- Typical results --.

Column 21,
Line 60, please insert -- Cloning of the V-Genes MAb32... --.

UNITED STATES PATENT AND TRADEMARK OFFICE
CERTIFICATE OF CORRECTION

PATENT NO. : 6,593,458 B1
DATED : July 15, 2003
INVENTOR(S) : Deborah A. Rathjen et al.

It is certified that error appears in the above-identified patent and that said Letters Patent is hereby corrected as shown below:

Column 22,
Line 36, please replace "asa" with -- as a --.

Column 23,
Line 33, please replace "CDNA" with -- cDNA --.
Line 40, please replace "HCM1OF" with -- HCM1FONO --.
Line 62, please replace "inall" with -- in all --.

Column 24,
Line 22, please replace "ofa" with -- of a --.
Line 33, please replace "expression VλCλ" with -- expression as VλCλ --.

Column 26,
Line 25, please replace "wer e" with -- were --.
Line 27, please replace "micewere" with -- mice were --.
Line 37, please replace "TAbs" with -- MAbs --.
Line 39, please replace "show n" with -- shown --.
Line 39, please replace "32 and 25" with -- 32 and 25, --.
Line 40, please replace "theuregion" with -- the region --.
Line 50, please replace "in viva" with -- in vivo --.
Line 50, please replace "andanti" with -- anti-viral --.

Column 28,
Line 23, please replace "matture" with -- mature --.

Signed and Sealed this

Eleventh Day of May, 2004

JON W. DUDAS
*Acting Director of the United States Patent and Trademark Office*